United States Patent [19]
McArdle

[11] Patent Number: 5,921,927
[45] Date of Patent: *Jul. 13, 1999

[54] POSITIONING METHOD AND APPARATUS FOR X-RAY TOMOGRAPHY

[75] Inventor: Phillip C. McArdle, Doncaster, Australia

[73] Assignee: Axialtome Australia Pty. Ltd., Australia

[*] Notice: This patent is subject to a terminal disclaimer.

[21] Appl. No.: 08/969,202

[22] Filed: Nov. 12, 1997

[51] Int. Cl.⁶ ...................................................... A61B 6/14
[52] U.S. Cl. ........................... 600/425; 600/426; 378/38; 378/39; 378/170; 378/206
[58] Field of Search ..................................... 600/425, 426, 600/429; 378/162, 170, 206, 38, 39, 205; 606/130

[56] References Cited

U.S. PATENT DOCUMENTS

| | | |
|---|---|---|
| 4,117,337 | 9/1978 | Staats . |
| 4,255,657 | 3/1981 | Lescrenier . |
| 4,293,771 | 10/1981 | Lescrenier . |
| 4,750,487 | 6/1988 | Zanetti . |
| 4,836,671 | 6/1989 | Bautista . |
| 4,846,173 | 7/1989 | Davidson . |
| 4,971,060 | 11/1990 | Schneider et al. . |
| 4,974,243 | 11/1990 | McArdle et al. . |
| 5,068,887 | 11/1991 | Hughes . |
| 5,165,410 | 11/1992 | Warne et al. . |
| 5,325,415 | 6/1994 | Coffman . |
| 5,431,162 | 7/1995 | McArdle . |

FOREIGN PATENT DOCUMENTS

| | | |
|---|---|---|
| 1021814 | 2/1953 | France . |
| 7904882 | 12/1980 | Netherlands . |

OTHER PUBLICATIONS

Gammex, Inc., Gammex Laser–Perfect Patient Positioning Systems introduces . . . , Gammex, 1981, Milwaukee, WI.

Primary Examiner—Ruth S. Smith
Attorney, Agent, or Firm—Feix & Feix

[57] ABSTRACT

A method and apparatus accurately positions the apparatus at a selected cranial implant site for x-ray tomography of the mandible and/or maxilla and the temporomandibular joint. The method and apparatus comprise making a stent of the mandible and/or maxilla of a patient and making a mark on the stent at a position that corresponds to the selected dental implant site. The stent is then positioned on a fixating device and the x-ray imaging apparatus is positioned with regard to tomographic imaging so that (a) the mark on the stent is at the intersection of the projected cross light beam and (b) the arm of the cross is aligned with the tangent of the dental arch at the site of interest. This positioning data is input to a program that will then operate the positioning motors and the x-ray source to project the tomographic images of the selected site. The projection of the temporomandibular joint is located by placing a basal view of the cranium on a flat plate located on the apparatus in the area of the projected cross and the relevant anatomical landmarks are then located and input to the program that will operate the positioning motors and x-ray source to project the tomographic images of the temporomandibular joints.

16 Claims, 31 Drawing Sheets

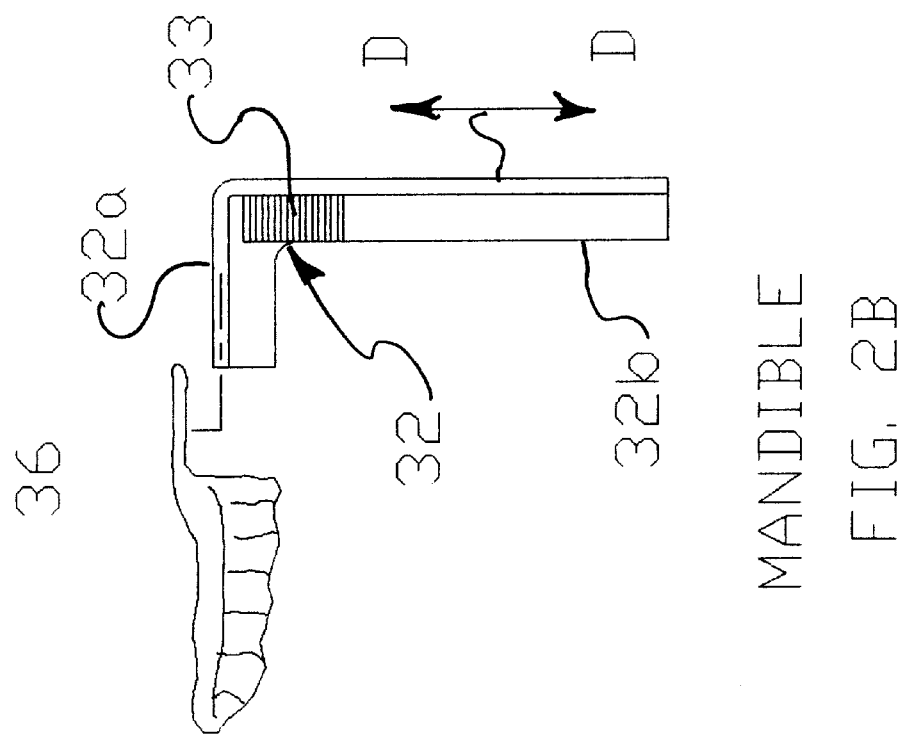
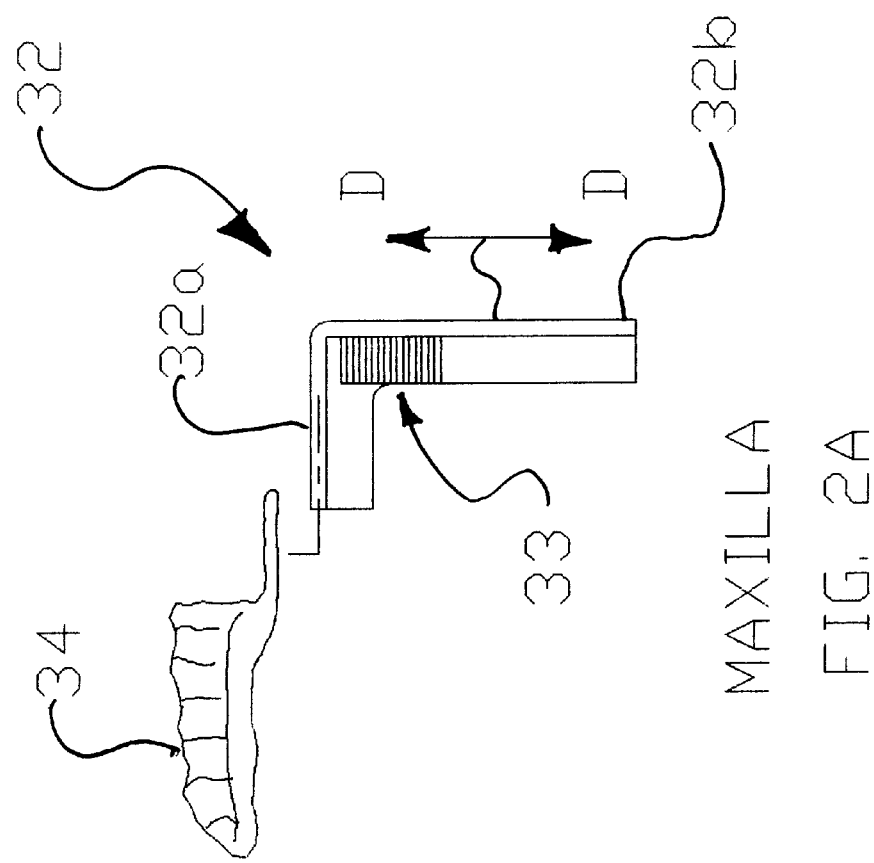

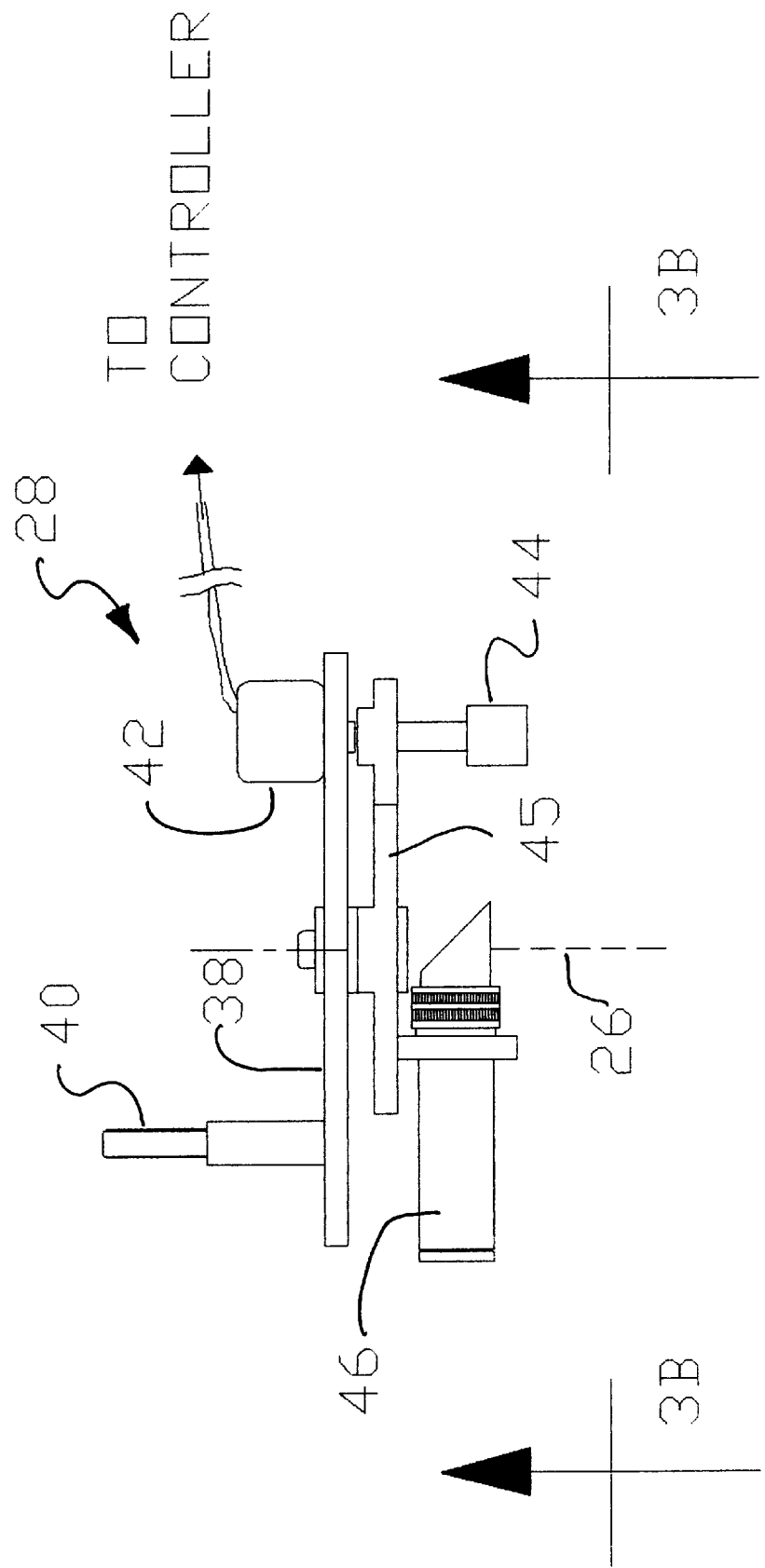

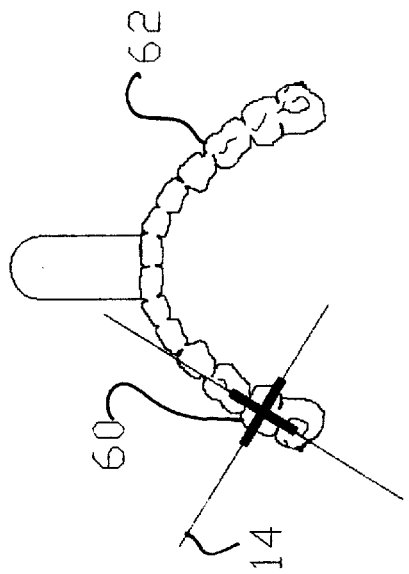
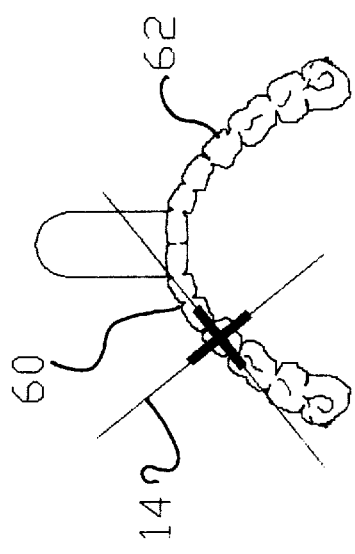
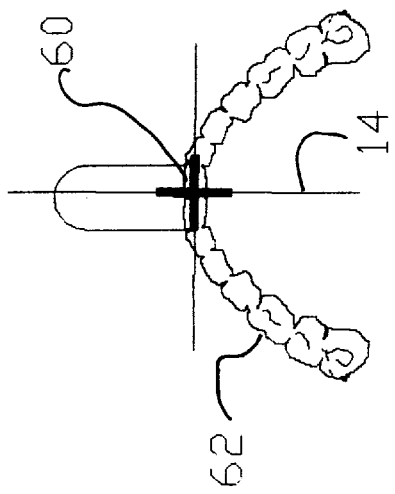
FIGURE 8E
FIGURE 8D
FIGURE 8C

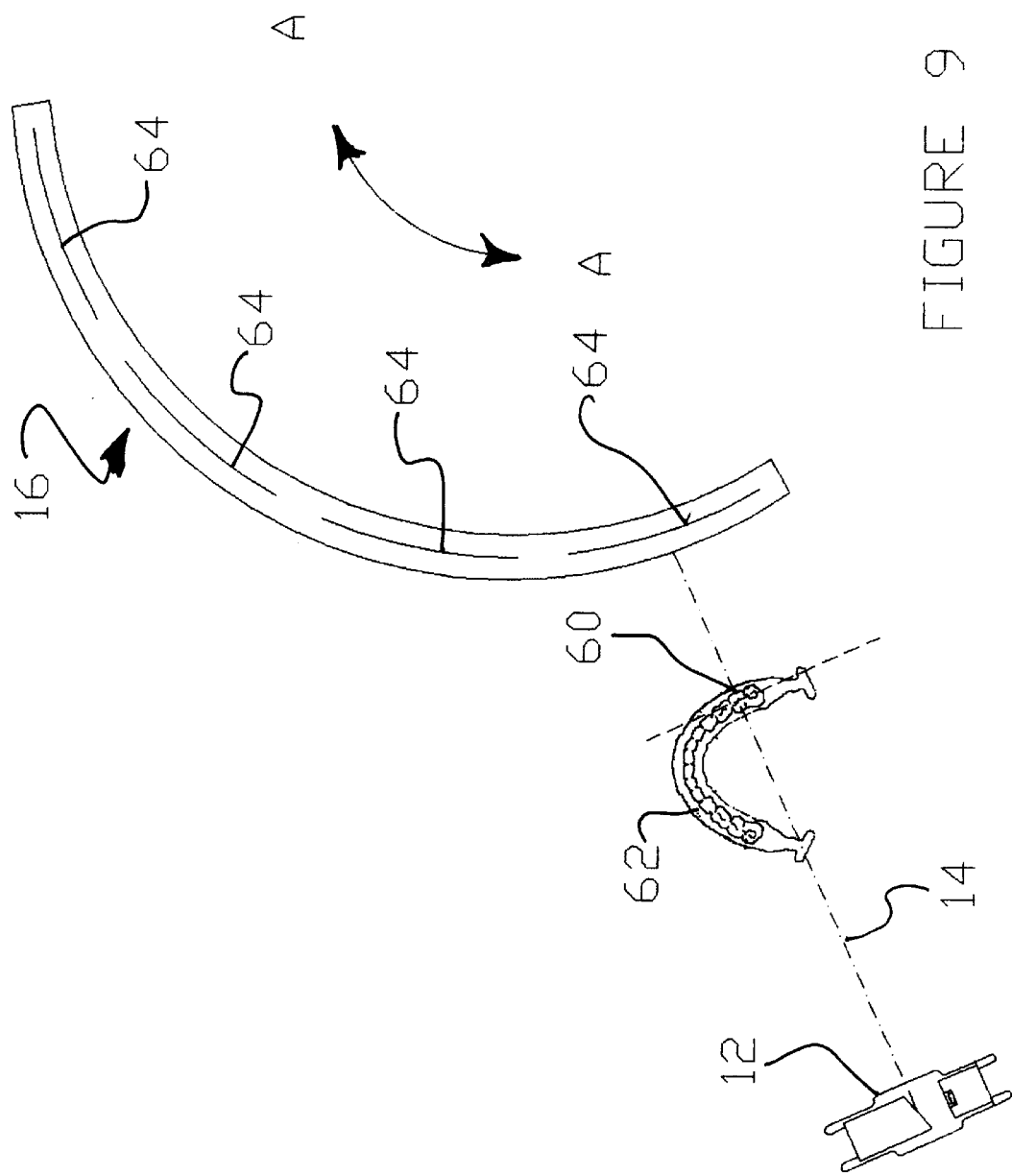

FIGURE 16B

X-RAY TOMOGRAPHIC IMAGING APPARATUS MOTOR DRIVE AND FUNCTION CONTROLLER SEQUENCE OF EVENTS AND SCREEN PRESENTATION

1. POWER ON
2. SCREEN:

TOMOGRAPH X-RAY SYSTEM

SETUP   IMPLANT TOMOGRAPHY   TMJ TOMOGRAPHY QUIT

3. IF SETUP IS SELECTED, THE SETUP SCREEN (FIG.15) APPEARS TO ENABLE USER TO ADJUST OPERATING PARAMETERS

4. WHEN "IMPLANT TOMOGRAPHY" IS SELECTED:

X,Y, ROTATION AND CASSETTE DRIVE
    DRIVE TO HOME POSITION
    THEN DRIVE TO TO THE START POSITION

5. SCREEN:

PLEASE WAIT WHILE MOTORS DRIVE INTO POSITION

6. WHEN MOTORS REACH THE START POSITION THE NEXT SCREEN APPEARS:

SET THE PROJECTOR TO ZERO AND PRESS ENTER

7. THE OPERATOR ADJUSTS LIGHT BEAM PROJECTOR ROTATION UNTIL "ZERO" LIGHTS, THEN PRESS ENTER.

8. THE NEXT SCREEN (FIG.15) APPEARS. OPERATOR THEN AFFIXES THE PATIENTS STENT ON THE STENT SUPPORT AND INPUTS EACH SECTOR WITH THE X, Y, AND THE ANGLE FOR ONE TO FIVE SECTORS.

9. SCREEN:

PLEASE WAIT WHILE MOTORS DRIVE INTO POSITION

ABOUT TO START FILMING

FIGURE 17A

X-RAY TOMOGRAPHIC IMAGING APPARATUS MOTOR DRIVE AND FUNCTION CONTROLLER SEQUENCE OF EVENTS AND SCREEN PRESENTATION

9. SCREEN:

INSERT THE FILM CASSETTE

POSITION THE PATIENT

PRESS CONTINUE WHEN READY

CONTINUE   CANCEL

10. SCREEN:

ABOUT TO START FILMING

11. MOTORS DRIVE INTO POSITION FOR FIRST SECTOR EXPOSURE SERIES.

12. SCREEN:
    PRESS THE EXPOSURE SWITCH WHEN READY

CANCEL

13. SCREEN:    SECTOR 1   SAGITTALL CUT
14. SCREEN:
    WARNING! THE X-RAY IS ON

SUPPORT ARM ROTATION DRIVE MOTOR DRIVES IN AN ARC PROGRAMMED IN THE SETUP SCREEN AND THE X-RAY IS TURNED ON FOR THE EXPOSURE PERIOD.

15. WHEN EXPOSURE HAS COMPLETED THE SCREEN APPEARS:

RELEASE BUTTON

ROTATION, X, Y, AND CASSETTE MOTORS DRIVE TO NEXT TOMOGRAPHIC POSITION

16. SCREEN:
    PRESS THE EXPOSURE SWITCH WHEN READY

CANCEL

FIGURE 17B

X-RAY TOMOGRAPHIC IMAGING APPARATUS MOTOR DRIVE AND FUNCTION CONTROLLER SEQUENCE OF EVENTS AND SCREEN PRESENTATION

17. SCREEN:
SECTOR 1 CROSS SECTIONAL CUT NO. 1

18. SCREEN:
WARNING! THE X-RAY IS ON

SUPPORT ARM ROTATION DRIVE MOTOR DRIVES IN AN ARC PROGRAMMED IN THE SETUP SCREEN AND THE X-RAY IS TURNED ON FOR THE EXPOSURE PERIOD.

19. WHEN THE EXPOSURE HAS COMPLETED THE SCREEN APPEARS:

RELEASE BUTTON

ROTATION, X, Y, AND CASSETTE MOTORS DRIVE TO THE NEXT TOMOGRAPHIC POSITION

20. SCREEN:
SECTOR 1 CROSS SECTIONAL CUT NO. 2

21. SCREEN:
WARNING! THE X-RAY IS ON

SUPPORT ARM ROTATION DRIVE MOTOR DRIVES IN AN ARC PROGRAMMED IN THE SETUP SCREEN AND THE X-RAY IS TURNED ON FOR THE EXPOSURE PERIOD.

22. WHEN THE EXPOSURE HAS COMPLETED THE SCREEN APPEARS:

RELEASE BUTTON

ROTATION, X, Y, AND CASSETTE MOTORS DRIVE TO THE NEXT TOMOGRAPHIC POSITION

23. SCREEN:
SECTOR 1 CROSS SECTIONAL CUT NO. 3

24. SCREEN:
WARNING! THE X-RAY IS ON

SUPPORT ARM ROTATION DRIVE MOTOR DRIVES IN AN ARC PROGRAMMED IN THE SETUP SCREEN AND THE X-RAY IS TURNED ON FOR THE EXPOSURE PERIOD.

FIGURE 17C

X-RAY TOMOGRAPHIC IMAGING APPARATUS MOTOR DRIVE AND
FUNCTION CONTROLLER SEQUENCE OF EVENTS AND SCREEN
PRESENTATION

25. WHEN EXPOSURE HAS COMPLETED THE SCREEN APPEARS:

RELEASE BUTTON

26. SCREEN:

SECTOR 1 COMPLETE. PLEASE WAIT WHILE MOTORS DRIVE TO NEXT POSITION

27. WHEN MOTORS REACH POSITION THE NEXT SCREEN APPEARS:

CHANGE THE FILM

PRESS CONTINUE WHEN READY

SECTOR I COMPLETE

CONTINUE

28. WHEN THE FILM HAS BEEN CHANGED, THE PATIENT POSITION HAS BEEN RECHECKED, AND CONTINUE SELECTED, THE SERIES IS REPEATED FROM (3) TO (27) FOR EACH SECTOR INPUT. AT THE COMPLETION OF ALL SECTORS INPUT A SCREEN APPEARS:

TOMOGRAPHS COMPLETE!

PRESS OK TO CONTINUE

OK

29. INITIAL SCREEN RETURNS AND SYSTEM IS NOW READY FOR NEXT EXAMINATION SERIES.

TOMOGRAPH X-RAY SYSTEM

SETUP   IMPLANT TOMOGRAPHY   TMJ TOMOGRAPHY   QUIT

FIGURE 17D

X-RAY TMJ TOMOGRAPHIC IMAGING APPARATUS MOTOR DRIVE AND
FUNCTION CONTROLLER SEQUENCE OF EVENTS AND SCREEN
PRESENTATION

1. POWER ON
2. SCREEN

TOMOGRAPH X-RAY SYSTEM

SETUP   IMPLANT TOMOGRAPHY  TMJ TOMOGRAPHY QUIT

3. IF SETUP IS SELECTED, THE SETUP SCREEN (FIG.15) APPEARS TO ENABLE USER TO ADJUST OPERATING PARAMETERS

4. WHEN "TMJ TOMOGRAPHY" IS SELECTED:

X,Y, ROTATION AND CASSETTE DRIVE
          DRIVE TO HOME POSITION
     THEN DRIVE TO TO THE START POSITION

5. SCREEN:

PLEASE WAIT WHILE MOTORS DRIVE INTO POSITION

6. WHEN MOTORS REACH THE START POSITION THE NEXT SCREEN APPEARS:

SET THE PROJECTOR TO ZERO AND PRESS ENTER

THE OPERATOR ADJUSTS LIGHT BEAM PROJECTOR ROTATION UNTIL "ZERO" LIGHTS,
                THEN PRESS ENTER.

7. THE NEXT SCREEN (FIG.15) APPEARS.

OPERATOR INSERTS THE FIL M PLATFORM TO THE PATIENT SUPPORT, THEN AFFIXES THE PATIENTS SUBMENTOVERTEX FILM ON FILM PLATFORM AND INPUTS EACH POSITION REQUESTED ON THE SCREEN. THE SELECTION OF A SAGITTALL OR OPEN VIEW OF THE CONDYLE IS REQUESTED PRIOR TO INPUTTING THE DATA. WHEN DATA IS ENTERED, START IS SELECTED.

8. SCREEN:

PLEASE WAIT WHILE MOTORS DRIVE INTO POSITION

ABOUT TO START FILMING

FIGURE 18A

X-RAY TMJ TOMOGRAPHIC IMAGING APPARATUS MOTOR DRIVE AND FUNCTION CONTROLLER SEQUENCE OF EVENTS AND SCREEN PRESENTATION

9. SCREEN:

INSERT THE FILM CASSETTE

POSITION THE PATIENT

PRESS CONTINUE WHEN READY

CONTINUE   CANCEL

PLANE FILM PLATFORM IS REMOVED, TMJ EAR POSTS INSERTED AND PATIENT IS POSITIONED ON THE PATIENT SUPPORT AND ADJUSTED INTO THE FRANKFORT PLANE.

10. SCREEN:

ABOUT TO START FILMING

11. MOTORS DRIVE INTO POSITION FOR FIRST SECTOR EXPOSURE SERIES.

12. SCREEN:

PRESS THE EXPOSURE SWITCH WHEN READY

CANCEL

13. SCREEN:

LEFT TMJ CROSS SECTIONAL CUT NO. 1

14. SCREEN:

WARNING! THE X-RAY IS ON

SUPPORT ARM ROTATION DRIVE MOTOR DRIVES IN AN ARC PROGRAMMED IN THE SETUP SCREEN AND THE X-RAY IS TURNED ON FOR THE EXPOSURE PERIOD.

15. WHEN EXPOSURE HAS COMPLETED THE SCREEN APPEARS:

RELEASE BUTTON

ROTATION, X, Y, AND CASSETTE MOTORS DRIVE TO NEXT TOMOGRAPHIC POSITION

16. SCREEN:

PRESS THE EXPOSURE SWITCH WHEN READY

CANCEL

FIGURE 18B

X-RAY TMJ TOMOGRAPHIC IMAGING APPARATUS MOTOR DRIVE AND
FUNCTION CONTROLLER SEQUENCE OF EVENTS AND SCREEN
PRESENTATION

17. SCREEN:
           LEFT TMJ CROSS SECTIONAL CUT NO. 2

18. SCREEN:
           WARNING! THE X-RAY IS ON

SUPPORT ARM ROTATION DRIVE MOTOR DRIVES IN AN ARC PROGRAMMED IN THE SETUP SCREEN AND THE X-RAY IS TURNED ON FOR THE EXPOSURE PERIOD.

19. WHEN THE EXPOSURE HAS COMPLETED THE SCREEN APPEARS:

RELEASE BUTTON

ROTATION, X, Y, AND CASSETTE MOTORS DRIVE TO THE NEXT TOMOGRAPHIC POSITION

20. SCREEN:
           LEFT TMJ CROSS SECTIONAL CUT NO. 3

21. SCREEN :
           WARNING! THE X-RAY IS ON

SUPPORT ARM ROTATION DRIVE MOTOR DRIVES IN AN ARC PROGRAMMED IN THE SETUP SCREEN AND THE X-RAY IS TURNED ON FOR THE EXPOSURE PERIOD.

22. WHEN THE EXPOSURE HAS COMPLETED THE SCREEN APPEARS:

RELEASE BUTTON

ROTATION, X, Y, AND CASSETTE MOTORS DRIVE TO THE NEXT TOMOGRAPHIC POSITION

23. SCREEN: IF OPEN SELECTED:

LEFT TMJ OPEN CROSS SECTIONAL CUT

POSITION PATIENT WITH MOUTH OPEN

FIGURE 18C

X-RAY TMJ TOMOGRAPHIC IMAGING APPARATUS MOTOR DRIVE AND FUNCTION CONTROLLER SEQUENCE OF EVENTS AND SCREEN PRESENTATION

SCREEN IF SAGITTALL SELECTED:

LEFT TMJ SAGITTAL CUT

POSITION PATIENT WITH MANDIBLE PROTRUDED

24. SCREEN :

WARNING! THE X-RAY IS ON

SUPPORT ARM ROTATION DRIVE MOTOR DRIVES IN AN ARC PROGRAMMED IN THE SETUP SCREEN AND THE X-RAY IS TURNED ON FOR THE EXPOSURE PERIOD.

25. WHEN THE EXPOSURE HAS COMPLETED THE SCREEN APPEARS:

RELEASE BUTTON

26. SCREEN:

LEFT TMJ COMPLETE. PLEASE WAIT WHILE MOTORS DRIVE TO NEXT POSITION.

27. WHEN MOTORS REACH POSITION THE NEXT SCREEN APPEARS:

CHANGE THE FILM

PRESS CONTINUE WHEN READY

LEFT TMJ COMPLETE

CONTINUE

28. MOTORS DRIVE INTO POSITION FOR RIGHT TMJ EXPOSURE SERIES.

29. SCREEN:
PRESS THE EXPOSURE SWITCH WHEN READY

CANCEL

FIGURE 18D

X-RAY TMJ TOMOGRAPHIC IMAGING APPARATUS MOTOR DRIVE AND FUNCTION CONTROLLER SEQUENCE OF EVENTS AND SCREEN PRESENTATION

30. SCREEN:

RIGHT TMJ CROSS SECTIONAL CUT NO. 1

WARNING! THE X-RAY IS ON

SUPPORT ARM ROTATION DRIVE MOTOR DRIVES IN AN ARC PROGRAMMED IN THE SETUP SCREEN AND THE X-RAY IS TURNED ON FOR THE EXPOSURE PERIOD.

31. WHEN EXPOSURE HAS COMPLETED THE SCREEN APPEARS:

RELEASE BUTTON

ROTATION, X, Y, AND CASSETTE MOTORS DRIVE TO NEXT TOMOGRAPHIC POSITION

32. SCREEN:
PRESS THE EXPOSURE SWITCH WHEN READY

CANCEL

X-RAY TMJ TOMOGRAPHIC IMAGING APPARATUS MOTOR DRIVE AND FUNCTION CONTROLLER SEQUENCE OF EVENTS AND SCREEN PRESENTATION

33. SCREEN:
RIGHT TMJ CROSS SECTIONAL CUT NO. 2
34. SCREEN:
WARNING! THE X-RAY IS ON

SUPPORT ARM ROTATION DRIVE MOTOR DRIVES IN AN ARC PROGRAMMED IN THE SETUP SCREEN AND THE X-RAY IS TURNED ON FOR THE EXPOSURE PERIOD.

35. WHEN THE EXPOSURE HAS COMPLETED THE SCREEN APPEARS:

RELEASE BUTTON

ROTATION, X, Y, AND CASSETTE MOTORS DRIVE TO THE NEXT TOMOGRAPHIC POSITION

FIGURE 18E

X-RAY TMJ TOMOGRAPHIC IMAGING APPARATUS MOTOR DRIVE AND FUNCTION CONTROLLER SEQUENCE OF EVENTS AND SCREEN PRESENTATION

36. SCREEN:

RIGHT TMJ CROSS SECTIONAL CUT NO. 3

37 SCREEN :

WARNING! THE X-RAY IS ON

SUPPORT ARM ROTATION DRIVE MOTOR DRIVES IN AN ARC PROGRAMMED IN THE SETUP SCREEN AND THE X-RAY IS TURNED ON FOR THE EXPOSURE PERIOD.

38. WHEN THE EXPOSURE HAS COMPLETED THE SCREEN APPEARS:

RELEASE BUTTON

ROTATION, X, Y, AND CASSETTE MOTORS DRIVE TO THE NEXT TOMOGRAPHIC POSITION

39. SCREEN: IF OPEN SELECTED:

RIGHT TMJ OPEN CROSS SECTIONAL CUT

POSITION PATIENT WITH MOUTH OPEN

SCREEN IF SAGITTALL SELECTED:

RIGHT TMJ SAGITTAL CUT

POSITION PATIENT WITH MANDIBLE PROTRUDED

40. SCREEN :

WARNING! THE X-RAY IS ON

SUPPORT ARM ROTATION DRIVE MOTOR DRIVES IN AN ARC PROGRAMMED IN THE SETUP SCREEN AND THE X-RAY IS TURNED ON FOR THE EXPOSURE PERIOD.

41. WHEN THE EXPOSURE HAS COMPLETED THE SCREEN APPEARS:

RELEASE BUTTON

FIGURE 18F

X-RAY TMJ TOMOGRAPHIC IMAGING APPARATUS MOTOR DRIVE AND FUNCTION CONTROLLER SEQUENCE OF EVENTS AND SCREEN PRESENTATION

42. SCREEN:

TMJ COMPLETE. PLEASE WAIT WHILE MOTORS DRIVE TO NEXT POSITION.

43. WHEN MOTORS REACH POSITION THE NEXT SCREEN APPEARS:

TOMOGRAPHS COMPLETE!

PRESS OK TO CONTINUE

OK

44. INITIAL SCREEN RETURNS AND SYSTEM IS NOW READY FOR NEXT EXAMINATION SERIES.

TOMOGRAPH X-RAY SYSTEM

SETUP   IMPLANT TOMOGRAPHY   TMJ TOMOGRAPHY   QUIT

FIGURE 18G

POSITIONING METHOD AND APPARATUS FOR X-RAY TOMOGRAPHY

FIELD OF THE INVENTION

The present invention relates to improvements in tomographic x-ray imaging apparatus and methods for use in dental professional offices. More particularly, the present invention is concerned with a method and an apparatus for accurately positioning a tomographic plane of an x-ray tomographic imaging apparatus to image multiple sites of interest on the mandible or maxilla of a patient without moving the head of the patient for each image exposure. The invention facilitates site evaluation of the mandible and the maxilla prior to installing osseointegrated implant posts to support various dental prostheses. The invention can be used to radiographically demonstrate the patients mandibular condyles and their relationship to the body of the mandible and the glenoid fossa.

BACKGROUND OF THE INVENTION

By way of background, the dental profession has been involved to an increasing degree with the well known osseointegrated implant system to facilitate dental prosthesis.

In order to properly install an implant, a tomographic x-ray of the proposed site should be taken so that the dentist can investigate the adequacy of the osseous tissue to support an implant post at the site of interest. The x-ray of the mandible or maxilla should employ tomography in order to project the cross-sectional area of the mandible or maxilla at the site of interest.

X-ray tomography, as is well known, involves rotating an x-ray source and a photographic plate in an arc relative to a patient during exposure of the x-ray image. Specifically, the x-ray source and the photographic plate are rotated through an arc about a central axis that is perpendicular to the x-ray beam. The vertical plane through the central axis is hereinafter referred to as the "tomographic plane." The result of such movement is that all bone structure in front of and behind the tomographic plane (i.e. on the sides toward and away from the plane of interest) are blurred and essentially do not appear in the image. Only the structure located at the tomographic plane appears in the x-ray image so that the image is of a cross section of the bone tissue. Therefore, by positioning the pivot point of the tomographic apparatus in a way such that the cross-sectional area that includes a particular site of interest of the mandible or maxilla of a patient will coincide with the tomographic plane, it is possible to obtain an x-ray image of the particular site of interest.

Clearly, an important consideration in the use of x-ray tomography is the accurate positioning of the anatomy of interest in the tomographic plane.

U.S. Pat. No. 4,974,423 entitled "Positioning System for X-Ray Tomography" and U.S. Pat. No. 5,431,162 entitled "Positioning Method and Apparatus for X-Ray Tomography", both commonly owned by this assignee of this application, disclose methods and apparatus for such accurate positioning of the head of a patient in relation to a tomographic apparatus which work effectively in many situations.

SUMMARY OF THE INVENTION

An object of the present invention is to provide an improved method and apparatus for positioning the head of a patient in relation to a tomographic apparatus.

Another object of the present invention is to provide an improved method and apparatus for positioning the tomographic plane of the apparatus on head of a patient in relation to the tomographic plane of the apparatus.

According to the present invention there is provided a method of positioning the tomographic plane of the apparatus on the head of a patient accurately for tomographic x-ray imaging of an implant site of a selected plane through a particular site of interest on the mandible or maxilla of the patient by means of a tomographic x-ray imaging apparatus, the x-ray tomographic imaging apparatus comprising an x-ray source and image receptor on an arm that is rotatable in an arc around a central axis and positionable in an X and Y plane to align the central axis with the anatomical site of interest, the method comprising:

a) forming a stent of the mandible or maxilla of the patient;

b) marking the stent at the positions of the stent which correspond with the sites of interest;

c) positioning the stent on a fixture that subsequently the patient can bite on the stent and be accurately positioned;

d) positioning the arm so that the projected light beam in the shape of a cross is located in the center of the selected site;

e) rotating the light beam projector so that an arm of the cross is tangent to the arc of the mandible or maxilla at the site of interest;

f) recording the position data of the site in step e);

g) repeating steps a) through f) for up to five sites on the selected mandible or maxilla; and h) positioning the patient on the stent and inserting a photographic plate in an image receptor for the x-ray source;

i) projecting the tomographic image of site in a sagittal plane;

j) projecting the tomographic image of the site in three cross-sectional planes spaced apart from each other at a desired interval; and l) replacing the photographic plate for projection of subsequent sites of interest up to a total of five sites.

It can readily be appreciated that once the patient has been positioned on the stent the timely imaging of up to five sites on the mandible or maxilla can be accomplished without moving the patient for each exposure. The four images on the photographic plate are aligned so that the mandibular canal readily visualized in the sagittal plane can be positionally projected to adjacent cross-sectional tomographic projections of the site and each cross-sectional slice can be evaluated for positional accuracy.

It is preferred that the mark(s) on the stent be radio opaque.

It is preferred that the marker be a metallic ball or other metallic plug inserted into the stent at the site(s) of interest.

It is preferred that the light beam project a cross and that the cross be rotated to provide the angle of the tangent of the dental arch at the site of interest by means of a digital encoder or a variable voltage controlled by a potentiometer connected to the rotating member of the light source to the controller.

The x-ray tomographic positioning apparatus for use in carrying out the above-described method comprises an x-ray source and image receptor on an arm that is rotatable in an arc around a central axis and positionable in an X and Y plane to align the central axis with the anatomical site of interest. The apparatus includes positioning motors for the X, Y, and rotational motor drive of the x-ray source, the image receptor support arm and the image receptor. The positioning motors are controlled by a program residing in a controller. The controller includes controls to effect the manual positioning of the tomographic x-ray plane through the particular site of interest on the patient's mandible and/or maxilla. The controller also includes a screen which provides instructions and status of events taking place in the examination to the clinician operating the apparatus.

In accordance with another aspect of the invention, it is possible to project a tomographic x-ray image of a selected plane through the temporomandibular joint (TMJ) of a patient. The objective of this projection is to radiographically demonstrate the patient's mandibular condyle and their relationship to the body of the mandible and the glenoid fossa.

According to the present invention there is provided a method of positioning the head of a patient accurately for tomographic x-ray imaging of the temporomandibular joint (TMJ) by means of the tomographic x-ray imaging apparatus described above and with additional enhancements. In this case, the controller further includes:

a) a setup program for the implant modality for user adjusted parameters, and:

b) a setup program for the TMJ and Ceph modality; and c) means for positioning the submentovertex projection of the patient's head on a platform so as to facilitate the entering the position data of the six points comprised of:
  1) the left radio opaque ear post marker;
  2) the left lateral pole of the condyle;
  3) the left medial pole of the condyle;
  4) the right medial pole of the condyle;
  5) the right lateral pole of the condyle; and
  6) the right radio opaque ear post marker.

Using the apparatus described above, the method comprising the steps of:

a) taking a basal projection of the patients cranium and processing the film;

b) positioning the projected film on a table affixed to the tomographic x-ray apparatus in a position that will enable the light projected cross to intersect the anatomical landmarks;

c) positioning the arm so that the projected light beam in the shape of a cross so that the intersection of the cross is located on the left ear post marker and entered;

d) positioning the arm so that the projected light beam in the shape of a cross is located on the left condyle lateral pole;

e) entering the position data for step d) into the controller;

f) repeating steps d) through e) for the left condyle medial pole, the right condyle medial pole, the right condyle lateral pole, and the right ear post marker;

g) removing the film and table, affixing the ear posts to the patient fixture;

h) positioning the patient on the fixture and placing ear posts in the external auditory canal;

i) inserting the photographic plate into holder;

j) exposing projections of the left temporomandibular joint in either the open mouth position or the sagittal view in the protruded jaw position, and three slices of the cross-section of the left joint in centric occlusion; and k) exposing projections of the right temporomandibular joint in either the open mouth position or the sagittal view in the protruded jaw position, and three slices of the cross-section of the left joint in centric occlusion.

It can readily be appreciated that once the patient has been positioned on the fixture the timely imaging of the four projections of the left and right temporomandibular joint can be accomplished without moving the patient for each exposure. The four images are imaged on the photographic plate.

It is preferred that the mark(s) on the ear posts for projecting the basal view be radio opaque.

It is preferred that the marker be a metallic ball or other metallic plug inserted into the ear post at the most extreme tip of the post.

It is preferred that the light beam project a line to delineate the Frankfort plane of the patient to assure correct positioning of the head prior to projecting the tomographic slice of the joint.

Methods and apparatus which incorporate the features described above and which are effective to function as described above constitute specific objects of this invention.

Other and further objects of the present invention will be apparent from the following description and claims and are illustrated in the accompanying drawings, which by way of illustration, show preferred embodiments of the present invention and the principles thereof and what are now considered to be the best modes contemplated for applying these principles. Other embodiments of the invention embodying the same or equivalent principles may be used and structural changes may be made as desired by those skilled in the art without departing from the present invention and the purview of the appended claims.

BRIEF DESCRIPTION OF THE DRAWINGS

The method and the apparatus of the present invention is described further by way of example with reference to the accompanying drawings in which:

FIG. 2A is a side elevation view of the patient stent (maxilla) and stent holder;

FIG. 2B is a side elevation view of the patient stent (mandible) and stent holder.

FIG. 3A is a side view of the light projection mechanism which is a component of the preferred embodiment of the tomographic imaging apparatus shown in FIG. 1;

FIGS. 8A–8E illustrates five hypothetical sites of interest on the patient stent;

FIG. 9 illustrates the positioning of the x-ray beam and image receptor (film cassette) at the proper angle and position for projecting a sagittal view of the site of interest;

FIG. 16B is an illustration of the screen display presented by the controller for the setup sequence;

FIGS. 17A–17D are an explanation of the sequence of program operations for the implant modality as it is to be incorporated in the operating manual for the tomographic device; and FIGS. 18A–18F are an explanation of the sequence of program operations for the TMJ modality as it is to be incorporated in the operating manual for the tomographic device.

DESCRIPTION OF THE PREFERRED EMBODIMENT

Figure 1:
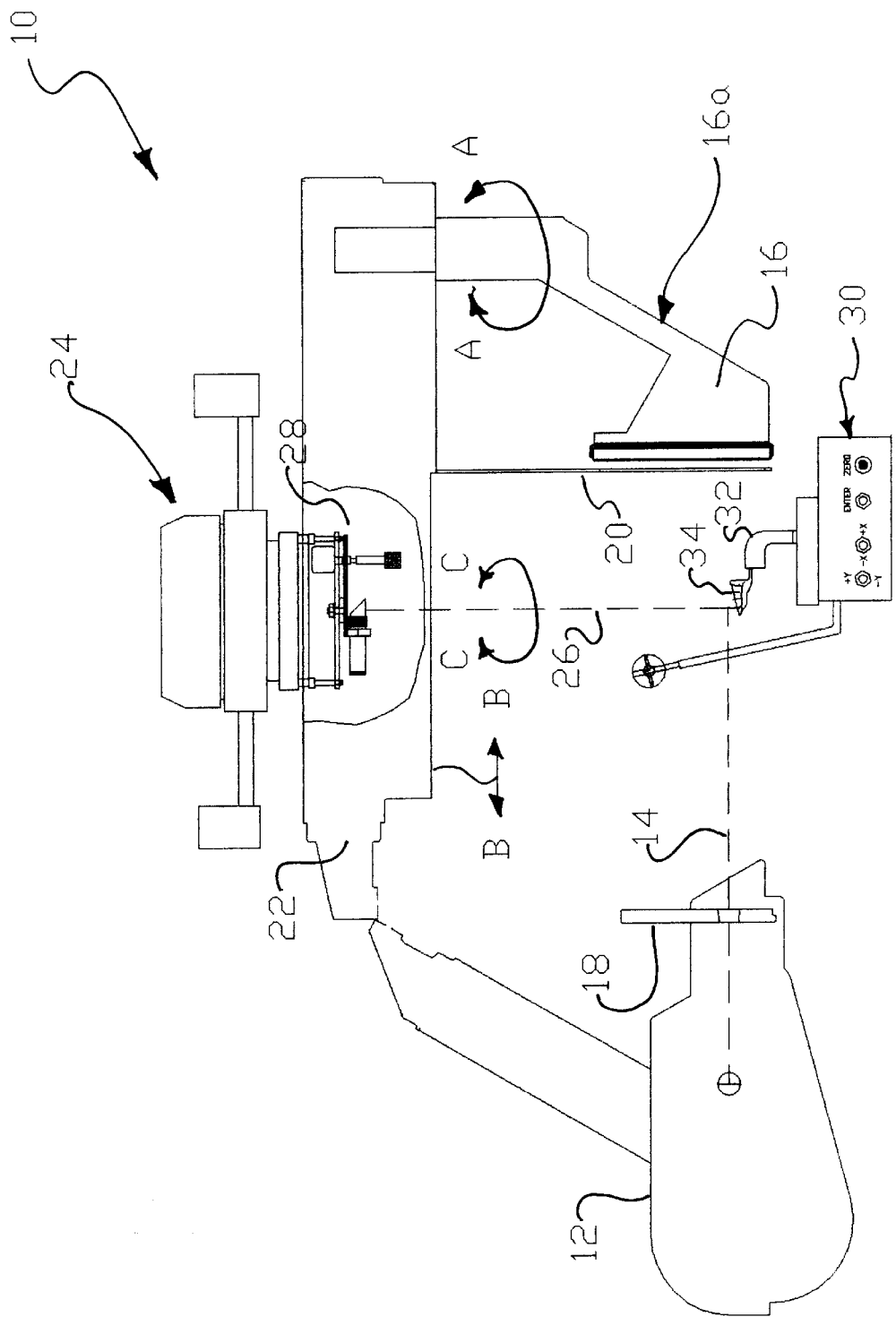
FIG. 1 is a schematic side elevation view showing a tomographic x-ray imaging apparatus in accordance with a preferred embodiment of the present invention.

An improved tomographic x-ray apparatus in accordance with one embodiment of the present invention is generally designated by reference numeral 10 in FIG. 1 The tomographic x-ray imaging apparatus 10 includes an x-ray source or tube assembly 12 for projecting a central x-ray beam 14 to an image receptor (film cassette) 16. A primary collimator 18 is provided to the x-ray source 12 and a secondary collimator 20 is provided to the image receptor 16.

The x-ray source 12 is supported on one end of spar or support arm 22 and the image receptor 16 is rotatably connected via image receptor support arm 16a to the other end of support arm 22, being rotatable about a vertical axis as indicated by directional arrow A—A. The support arm 22 is coupled to a programmable positioning or drive assembly 24 for effecting the necessary X, Y translational and rotational positioning of the support arm 22 (and x-ray source 12 and image receptor 16) relative to a central vertical axis 26. Translational movement along one of the X, Y axes is indicated by directional arrow B—B (movement along the other of the X, Y axes is normal to the page). Rotational movement of the support arm 22 is indicated by directional arrow C—C.

Also shown is a light beam projection assembly 28 and a patient support assembly or patient fixator 30. The patient fixator 30 supports a stent (in this case a maxilla stent). The drive assembly 24 and patient fixator 30 are affixed to a carrier (not shown) that is raised and lowered to the proper height on a vertical column (not shown). The patient fixator 30 includes the controls for the X, Y and rotation movement of the drive assembly 24.

The tomographic x-ray imaging apparatus 10 is operable to rotate the x-ray source 12 and x-ray beam (indicated by the dotted line 14) in an arc programmed for the particular imaging modality at the site of interest (typically 6 degrees for the sagittal plane and 40 degrees for the cross section), about the central axis 26 to produce an x-ray image of a tomographic plane extending vertically through the central axis 26. Therefore, by positioning the x-ray source 12 so that a particular site of interest on the mandible or maxilla of the patient is positioned in the tomographic plane, it is possible to produce a tomographic image through the site of interest.

In this connection, the positioning apparatus in accordance with the preferred embodiment of the present invention is operable in relation to the tomographic x-ray imaging apparatus shown in the figures to so position the apparatus on the head of the patient.

The positioning apparatus is based on the use of a stent holder and stent of the mandible or maxilla of the patient (see FIGS. 2A–2B) which is marked in an appropriate way, typically by means of a radio opaque marker (not shown) such as a metallic ball, to indicate a particular site of interest. FIG. 2A shows stent holder assembly 32 supporting a maxilla stent 34. FIG. 2B shows stent holder assembly 32 supporting a mandible stent 36. In accordance with a preferred embodiment of the invention, the stent holder assembly 32 comprises two pieces 32a and 32b, each with a matching serrated edge region (indicated generally by reference numeral 33). In use, the top section 32a is inserted into the bottom section 32b and is pressed down until the stent (34 or 36) is clamped securely between the two sections (clamp structure is not shown). The stent holder assembly is designed to position the stent at the correct height when inserted into the support mechanisim.

Figure 3B:
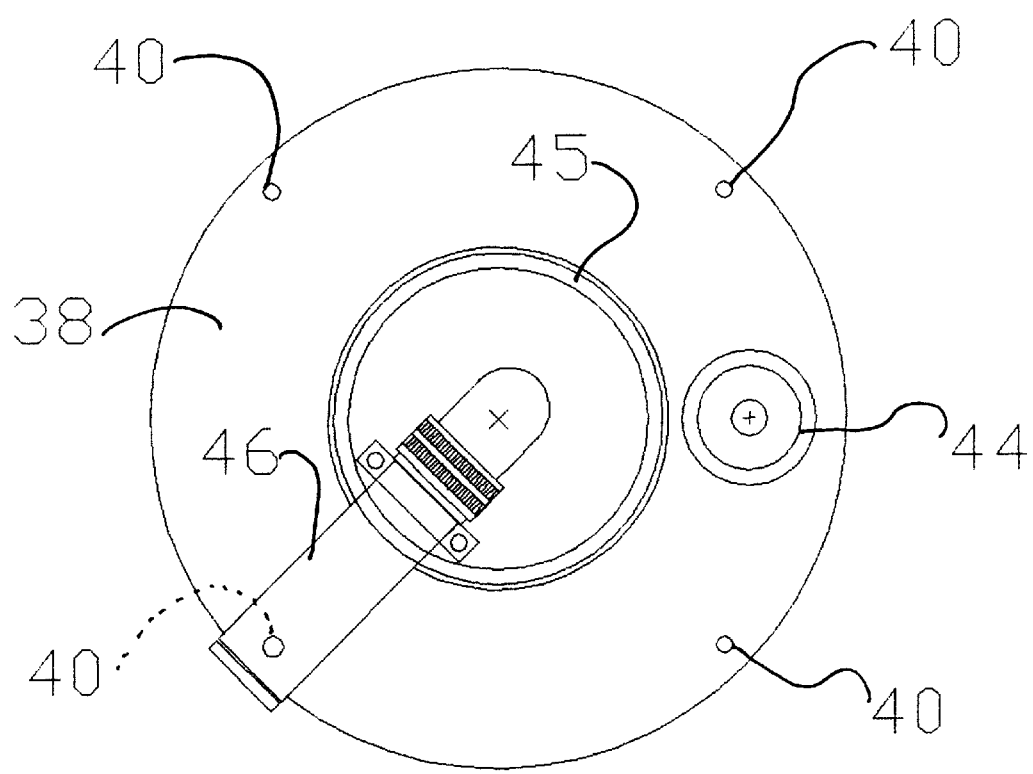
FIG. 3B is a bottom (underside) view of the light projection mechanism taken along the line and in the direction of arrows 3B—3B of FIG. 3A.
Figure 4:
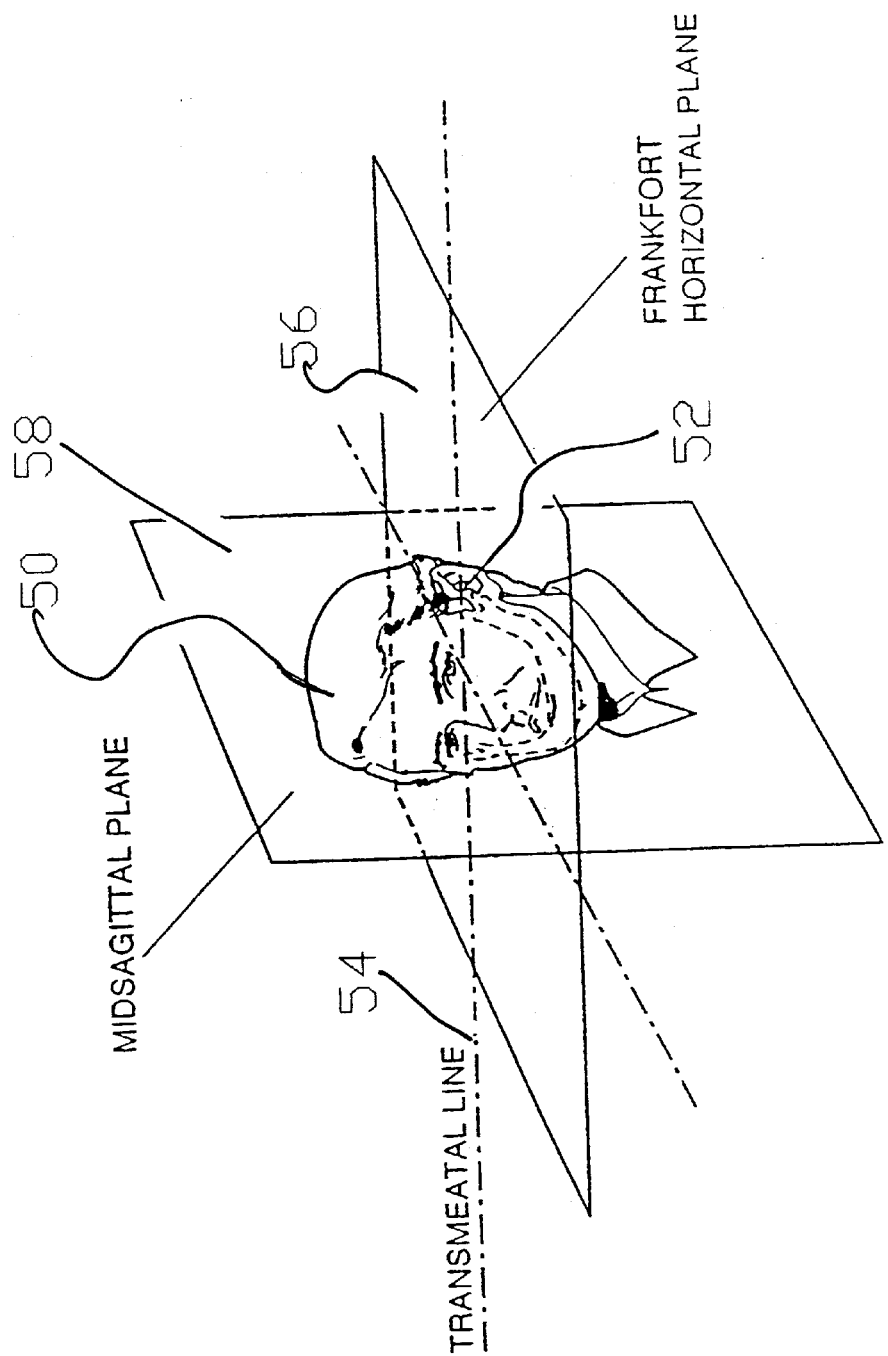
FIG. 4 is a schematic view showing a patient's head and illustrating the midsagittal plane of the head as well as the transmeatal line and the Frankfort Horizontal plane, which are relevant to the method and apparatus of the invention.

With reference to FIGS. 3A–3B, the details of the light beam projection assembly 28 will now be described. The light beam projection assembly 28 includes apparatus support studs 40 (only one of four shown in FIG. 3A for clarity) for securing a disk-shaped support platform 38 of the assembly 28 to the support arm 22 (see FIG. 1), a position encoder 42, rotation control 44, support arm 45, and a light source 46 for projecting a light beam 26 to a mark formed on the stent (see e.g., FIG. 1). Rotation control 44 is used to rotate support arm 45 and the light source 46 about a central vertical axis colinear with the light beam 26. In a preferred embodiment of the invention, the light source 46 is a laser projector which projects a coherent beam of light in the shape of a cross down onto a mark on the stent. The light beam may also comprise an incandescent light source FIG. 4 shows several reference plane and lines of the human cranium as they are defined medically. These planes and lines are useful as references in aligning the tomographic plane of the x-ray tomographic imaging apparatus with respect to the head 50 of the patient and in the discussion of the invention which follows.

The ear cavities 52 define the external auditory meatus, with a horizontal line passing through these points 52 defined as the transmeatal line 54. A horizontal plane passing through the transmeatal line and through the floor of the orbit is defined as the Frankfort horizontal plane 56. A vertical plane 58 passing through the center and bisecting the head including the nose is called the midsagittal plane. Another horizontal plane is the plane that intersects the occlusal surfaces of the teeth and is called the occlusal plane (not shown in FIG. 4).

In accordance with the present invention, some of these planes and lines are used to reference the position of the patient in the x-ray tomography apparatus and to define and determine a measured correction of the patient's cranial position in X, Y, Z coordinates and rotational position about a vertical axis.

Figure 5:
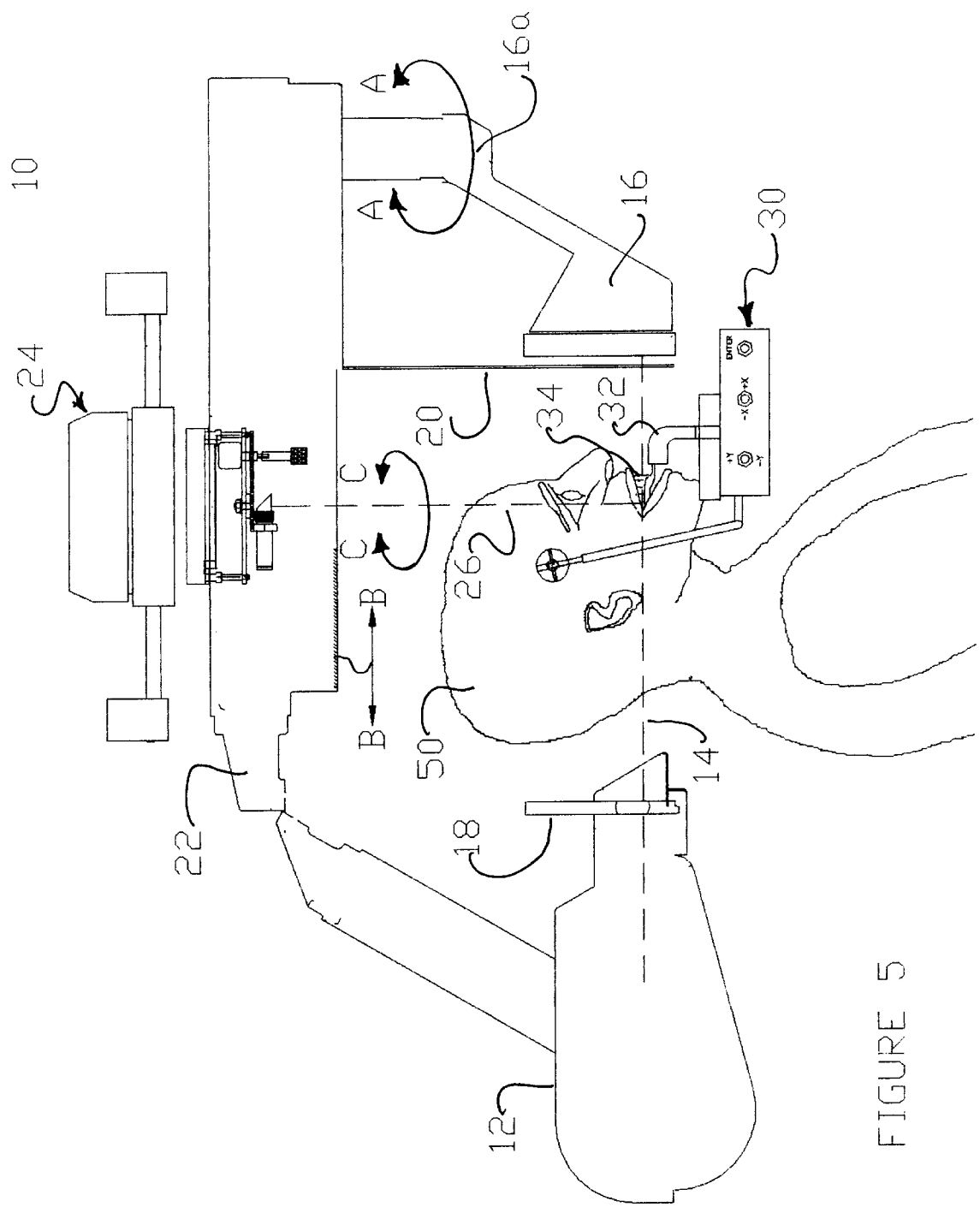
FIG. 5 is a side view of the tomographic apparatus illustrating the positioning of a patient in relation to the central beam of the x-ray and the projection of the light in the shape of a cross that indicates the center of rotation of the x-ray apparatus.

FIG. 5 is a side view of the tomographic x-ray imaging apparatus 10 illustrating the positioning of a patient's head 50 in relation to the central beam 14 of the x-ray source 12 and the projection of the light beam 26 in the shape of a cross that indicates the center of rotation of the tomographic x-ray imaging apparatus 10.

Figure 6:
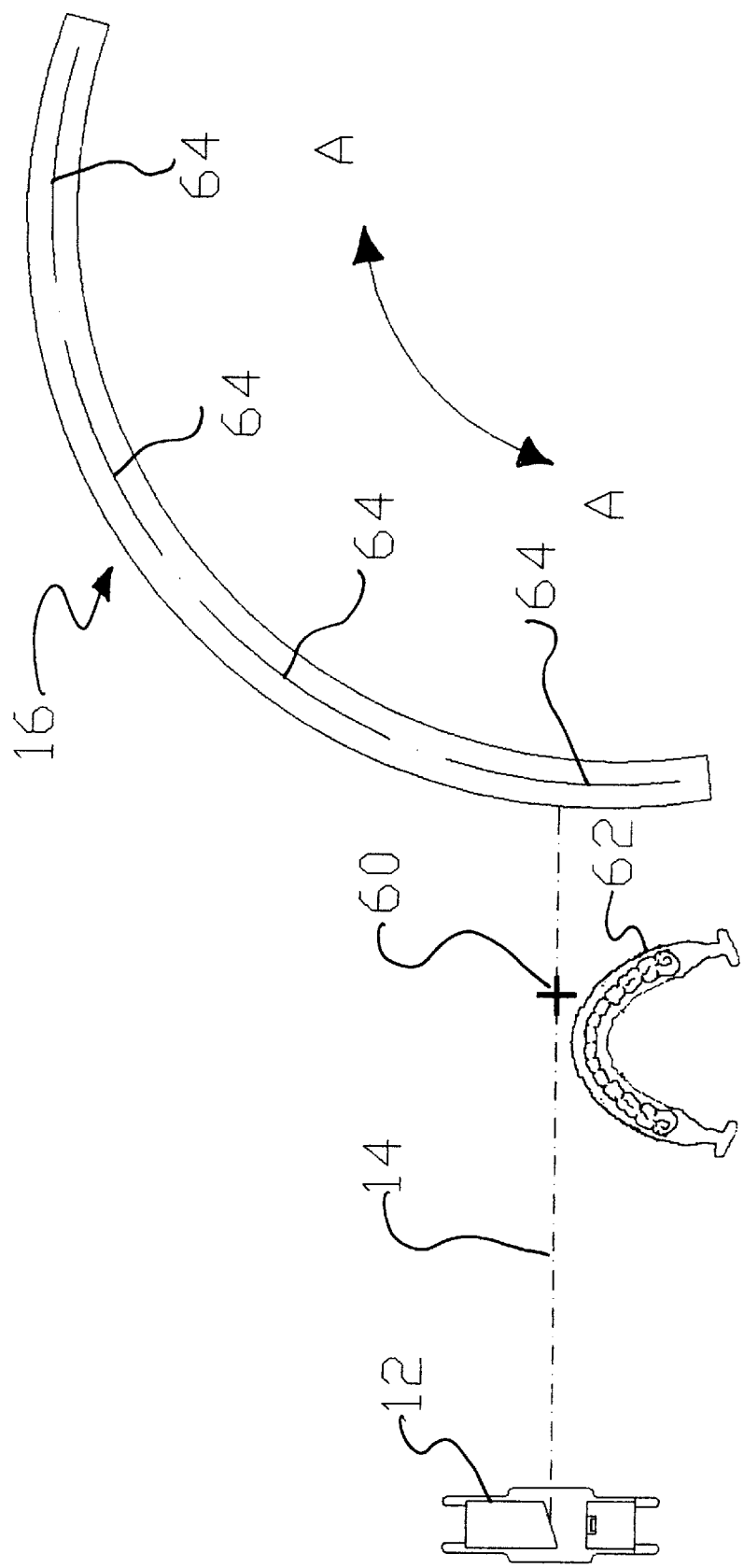
FIG. 6 illustrates the relationship of the x-ray source, the film cassette, the center of rotation of the x-ray apparatus and the patient's mandible.
Figure 11:
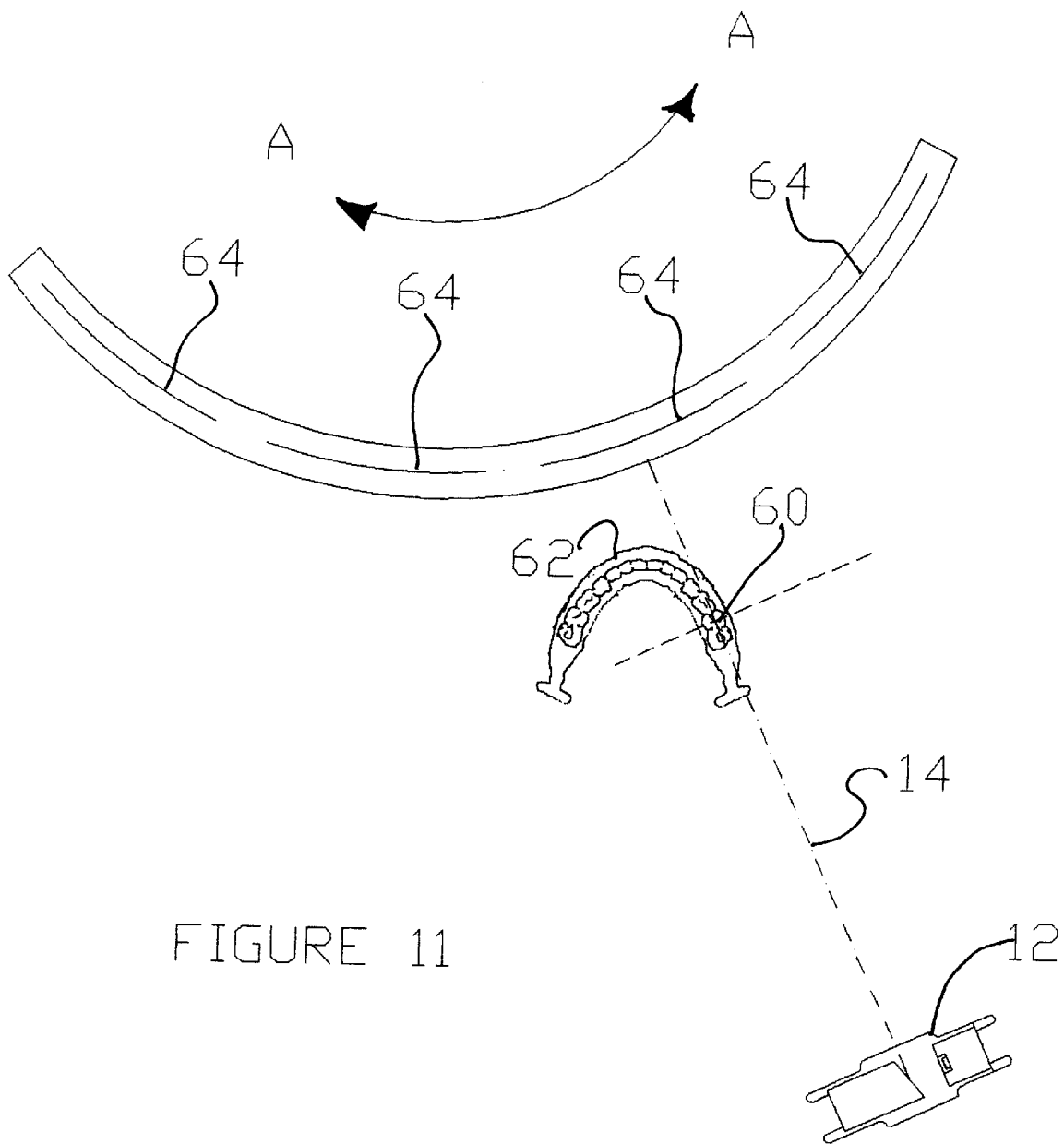
FIG. 11 illustrates the positioning of the x-ray beam and image receptor (film cassette) at the proper angle and position for projecting the cross sectional view of the site of interest.

FIGS. 6, 9 and 11 illustrate the relationship of the x-ray source 12, the line indicating the central axis of the x-ray beam 14, the image receptor 16, the center of rotation of the tomographic x-ray imaging apparatus (indicated by the projected light beam in the shape of a cross 60), and the patient mandible 64. In the preferred embodiment of the invention, the image receptor 16 is a film cassette and has a minimum of four exposure regions 64. In use, the film cassette is rotated between exposures to advance to the next exposure region.

Figure 7B:
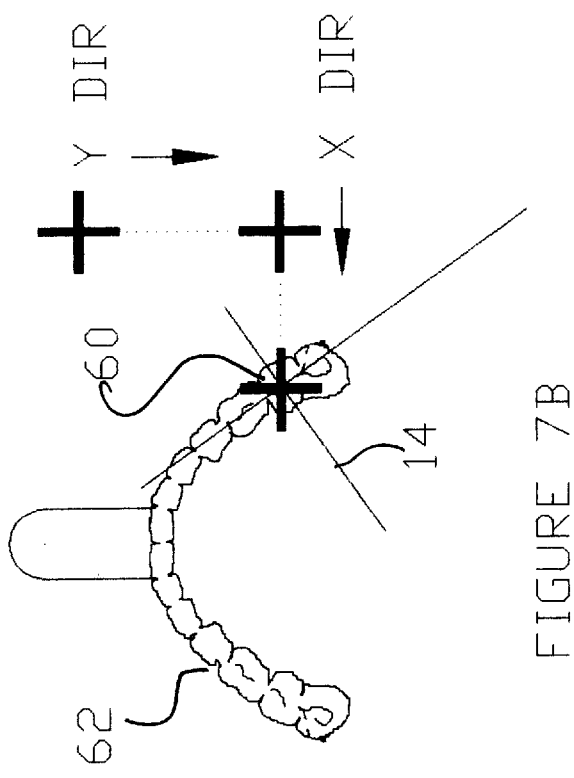
FIGS. 7A–7C illustrate the patient's stent in a reference start position for measuring the location of a site of interest for x-ray tomography (FIGS. 7A), the X and Y axis positioning movement (FIG. 7A) and rotational movement (FIG. 7C) that positions the point of rotation at the anatomical site of interest and indicates the angle of the dental arch for the film (image) plane.
Figure 7C:
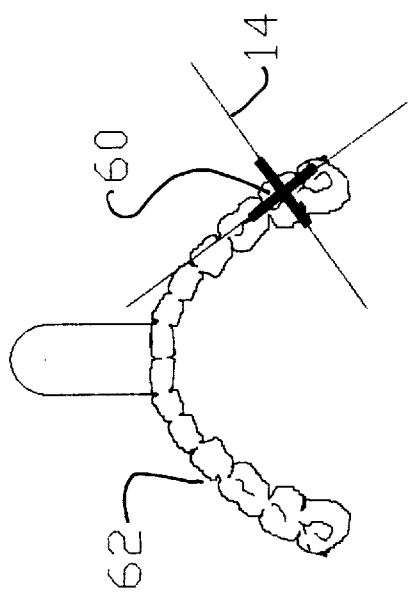
Figure 7A:
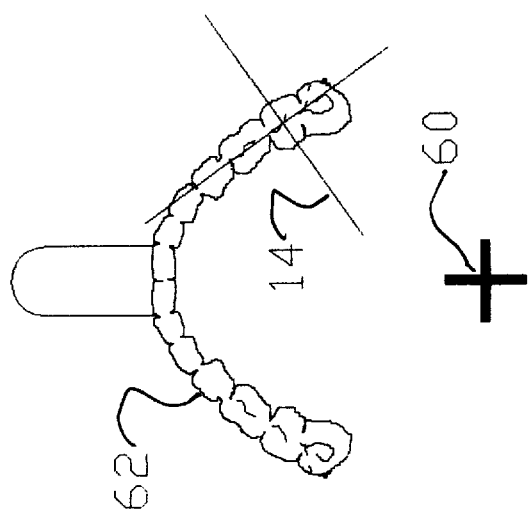
Figure 8B:
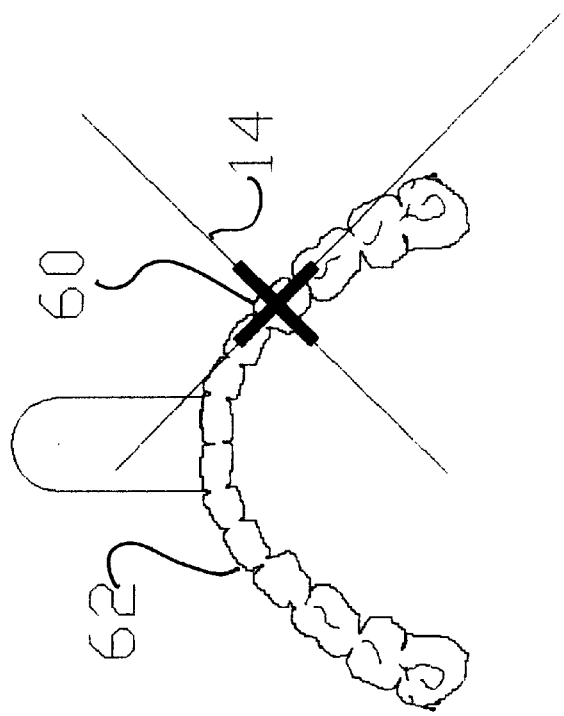
Figure 8A:
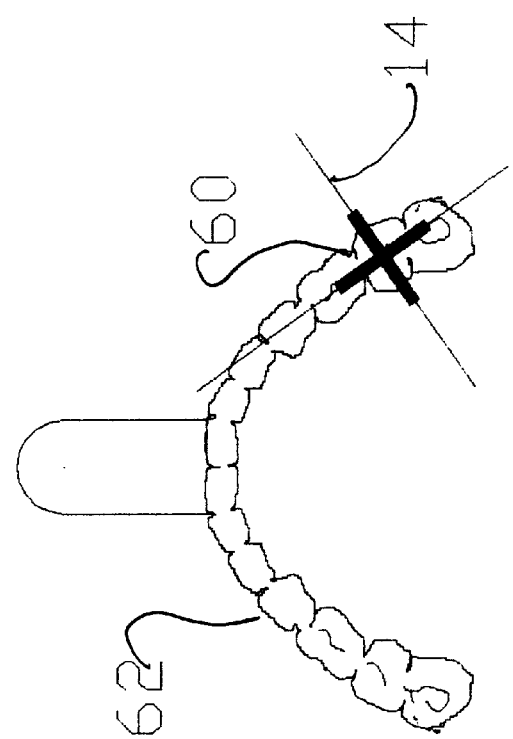

FIGS. 7A–7C illustrate the X, Y and rotational movement of the drive assembly 24 for positioning the center or point of rotation of the tomographic x-ray imaging apparatus 10 (i.e. projected cross 60) at an anatomical site of interest. The apparatus is positioning such that the image plan (i.e. film plane) is parallel to a tangent of the dental arch 62 at a particular anatomical site of interest. FIGS. 8A–8E illustrate how the projected cross 60 is positioned relative to the dental arch 62 at five hypothetical sites of interest.

Figure 10:
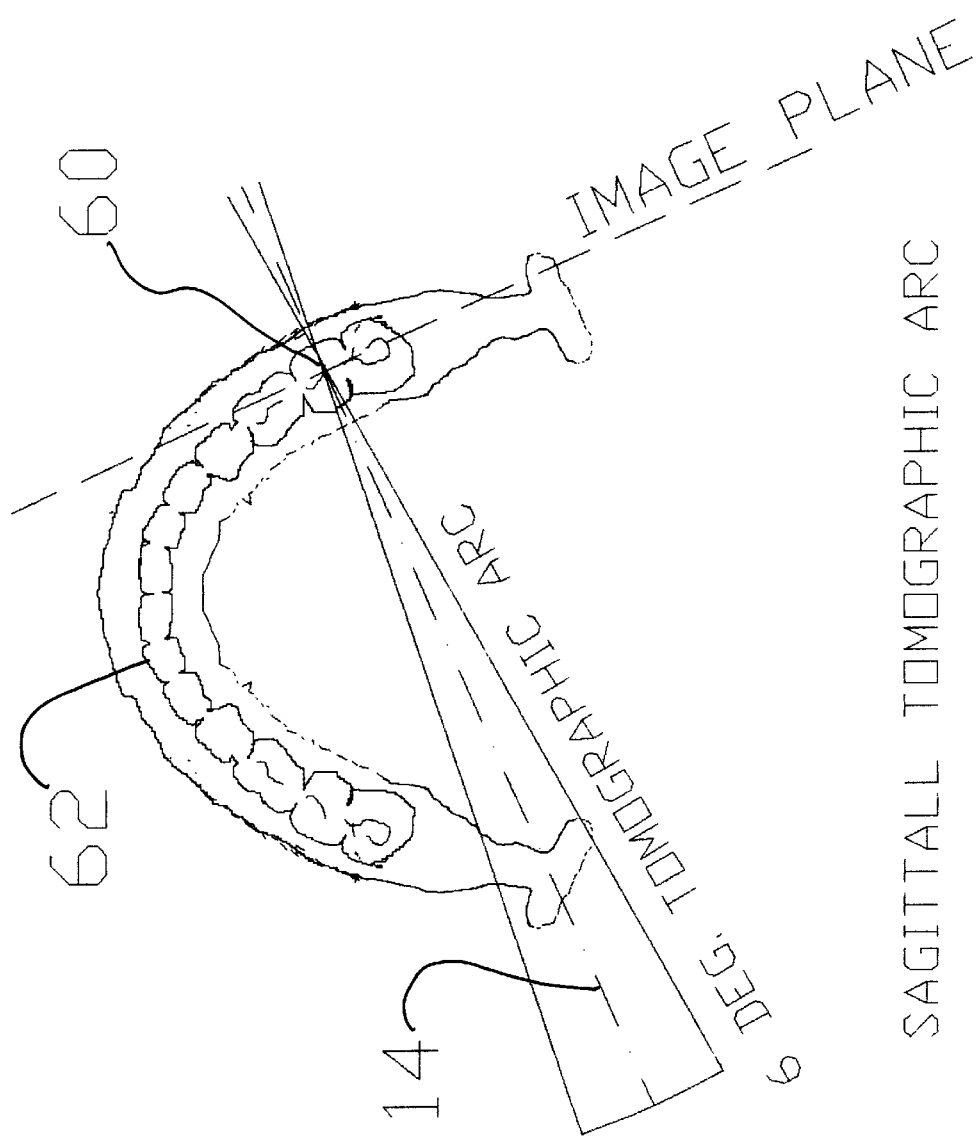
FIG. 10 illustrates the tomographic arc at the site of interest to project the sagittal view of the site of interest.

FIG. 10 illustrates the tomographic arc at a particular site of interest to project the sagittal view of the site of interest. FIG. 11 illustrates the positioning of the x-ray source 12 and image receptor 16 at the proper angle and position for projecting the cross sectional view of a particular site of interest.

Figure 12:
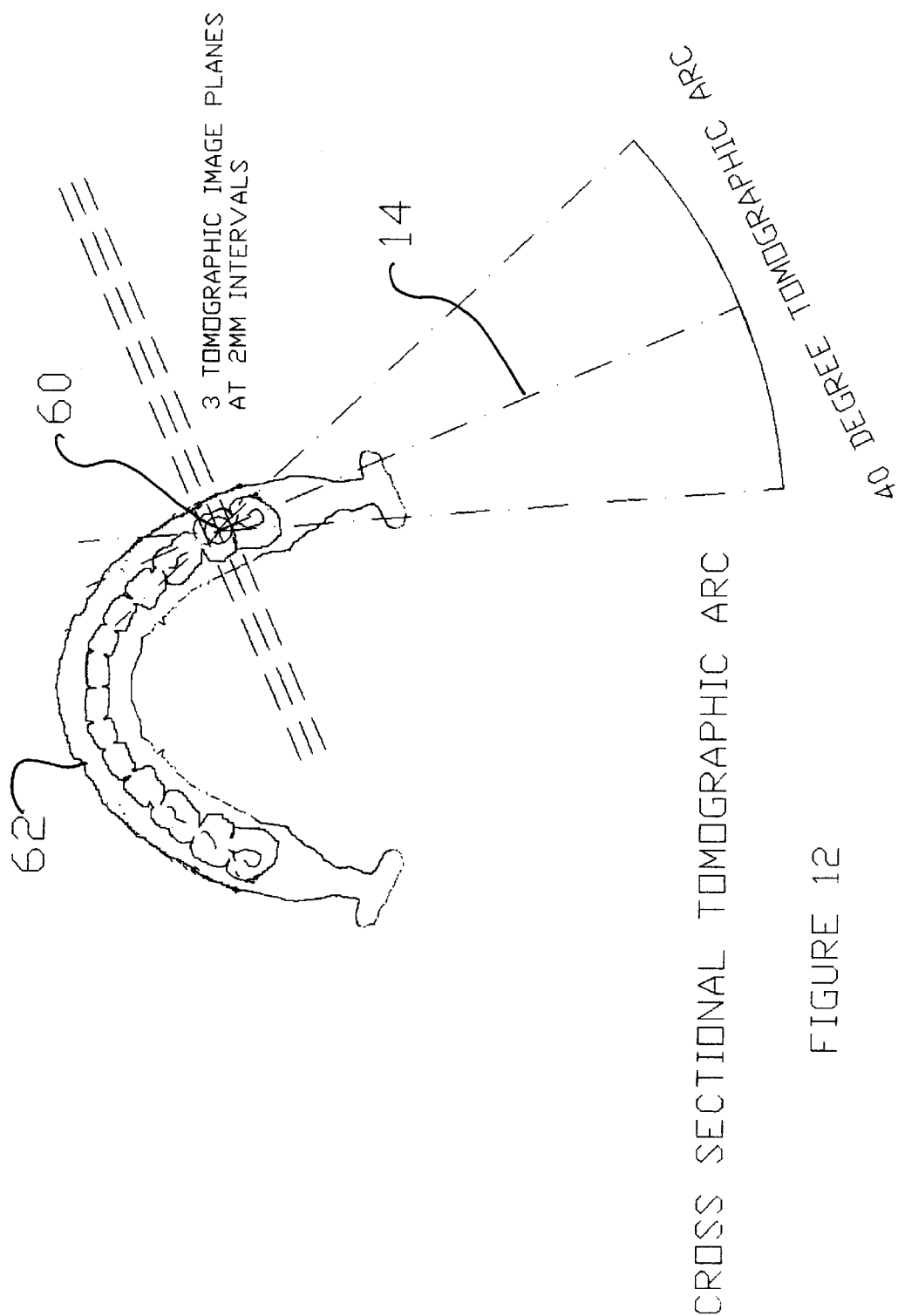
FIG. 12 illustrates the tomographic arc at the site of interest to project the cross sectional view of the site of interest and illustrates three image planes spaced apart at a hypothetical two millimeter interval spacing.

FIG. 12 illustrates the tomographic arc at a particular site of interest to project the cross sectional view of the site of interest and illustrate three additional image planes at a hypothetical two millimeter spacing. In accordance with a method aspect of the present invention, the resulting four images on the photographic plate can be aligned so that the mandibular canal readily visualized in the sagittal plane can be positionally projected to adjacent cross-sectional tomographic projections of the site of interest and each cross-sectional slice can be evaluated for positional accuracy.

The tomographic x-ray imaging apparatus 10 is positionable so that the light beam projection assembly 28 is able to project a light beam in the shape of a cross 26 that intersects both the central beam 14 from the x-ray source 12 and a mark on the stent (maxilla or mandible) that is supported by stent support 32 on the patient fixator 30. The stent is marked at several places (up to a total of five places), each place corresponding to an anatomical site of interest. The patient fixator 30 includes positioning controls for effecting the necessary X, Y, and rotational positioning of the drive assembly 24, light beam projection assembly 28, and image receptor relative to each mark on the stent. In accordance with a preferred embodiment of the invention, a radio opaque marker such as a steel ball is used to mark the stent at the site(s) of interest. The apparatus is positioned on the site of interest so that the tomographic plane extending vertically through the central axis 26 coincides with the site of interest.

For each site of interest on the stent, the light beam projection assembly 28 is rotated about the central vertical axis 26 by manipulation of rotational control 44 such that a first arm of the projected cross 60 is parallel to the central x-ray beam axis 14 and a second arm is co-planar with the tomographic plane (see FIGS. 6–11). In this connection, it can readily be appreciated that the light beam, when projected onto the surface of the stent provides a readily identifiable means of assessing the position of the stent with respect to the marking on the stent which indicates the particular site of interest of the mandible or maxilla of the patient.

In the use of the apparatus described above, a clinician prepares a stent of the patient's mandible and/or maxilla in an appropriate manner and includes radio opaque markers to indicate the particular site(s) of interest on the mandible or maxilla, for example, for an osseointegrated implant post. The stent is then located in the stent holder or stent support 32 and the various sites indicated are then encoded into the controller in accordance with the instructions that are presented on the controller screen. The patient is then positioned on the stent (see FIG. 5), and the sites tomographically projected on the film. By inspection of the x-ray image the clinician can determine whether the site of interest is acceptable for receiving an osseointegrated implant post.

Figure 13:
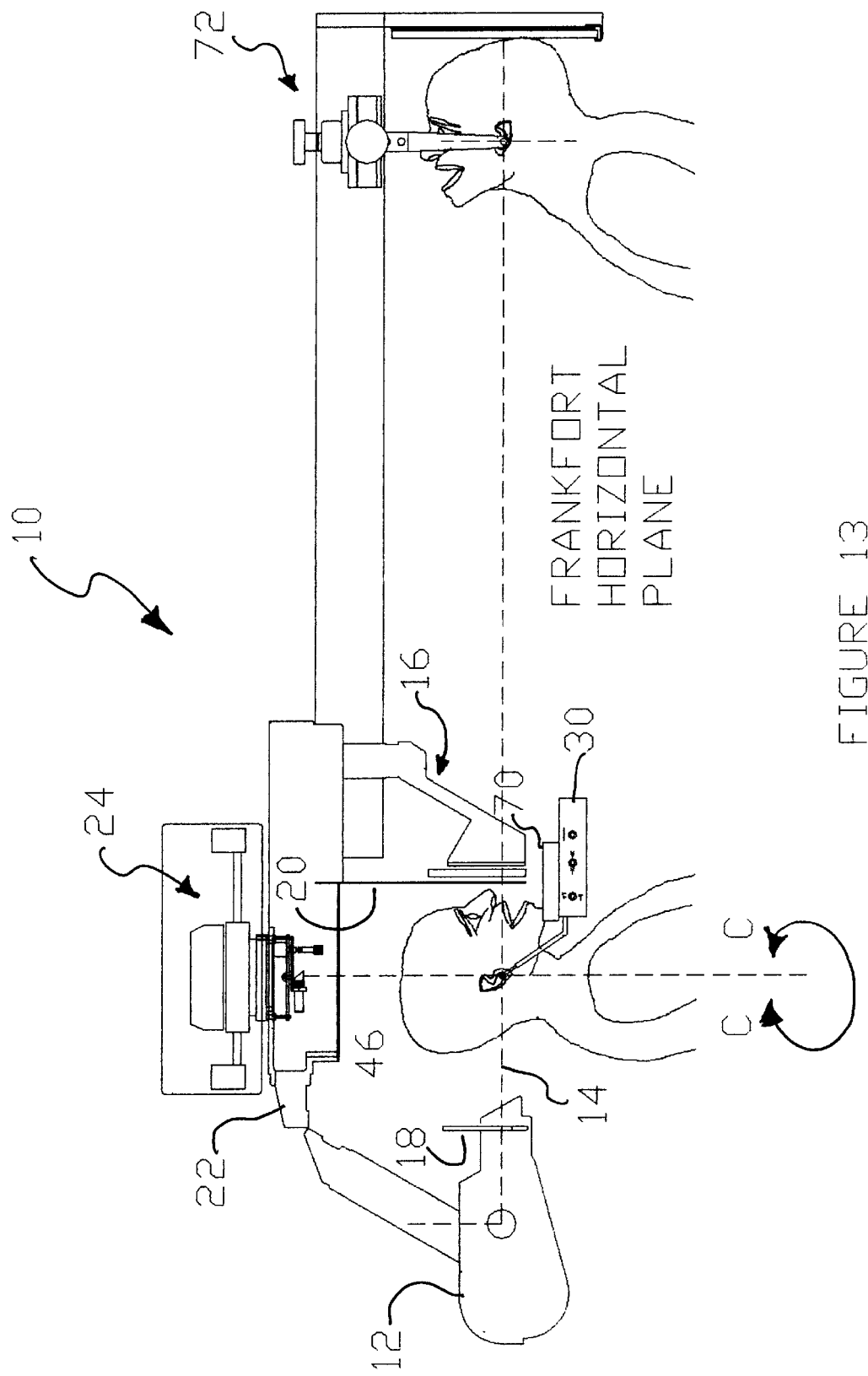
FIG. 13 is a side view of the preferred embodiment of FIG. 1 shown including a cephalometric apparatus with a patient in the submentovertex position for the basal view and in position for the tomographic imaging of the TMJ.
Figure 14:
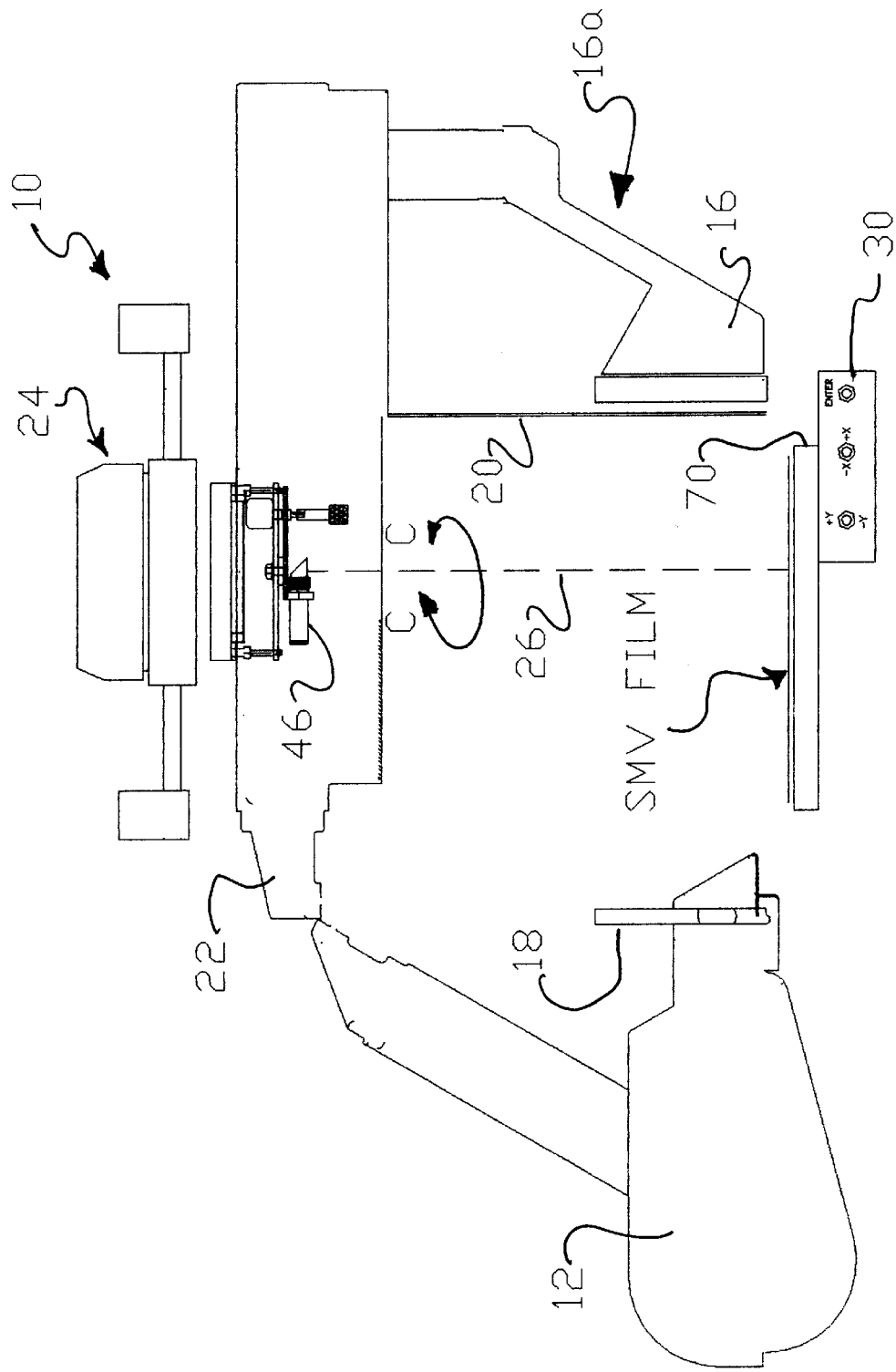
FIG. 14 is a side view of an alternate embodiment of the invention similar to that shown in FIG. 1 except that the stent support base is replaced with the basal film table suitable for providing basal, or submentovertex view information to the controller.

A tomographic x-ray imaging apparatus in accordance with another embodiment of the invention is shown in FIGS. 13–14 and is designated generally by reference numeral 10'. The tomographic x-ray imaging apparatus 10' is essentially identical to the tomographic x-ray imaging apparatus 10 shown and described in the previous Figures except that the stent support 32 is replaced by a basal film table 70.

The embodiment shown in FIG. 13 further includes a cephalometric apparatus 72 attached to the tomographic x-ray imaging apparatus 10'. The left side of the figure shows a patient in the submentovertex position for making a basal view projection. The right side of the figure shows a patient in position for the tomographic imaging of the TMJ.

Figure 15:
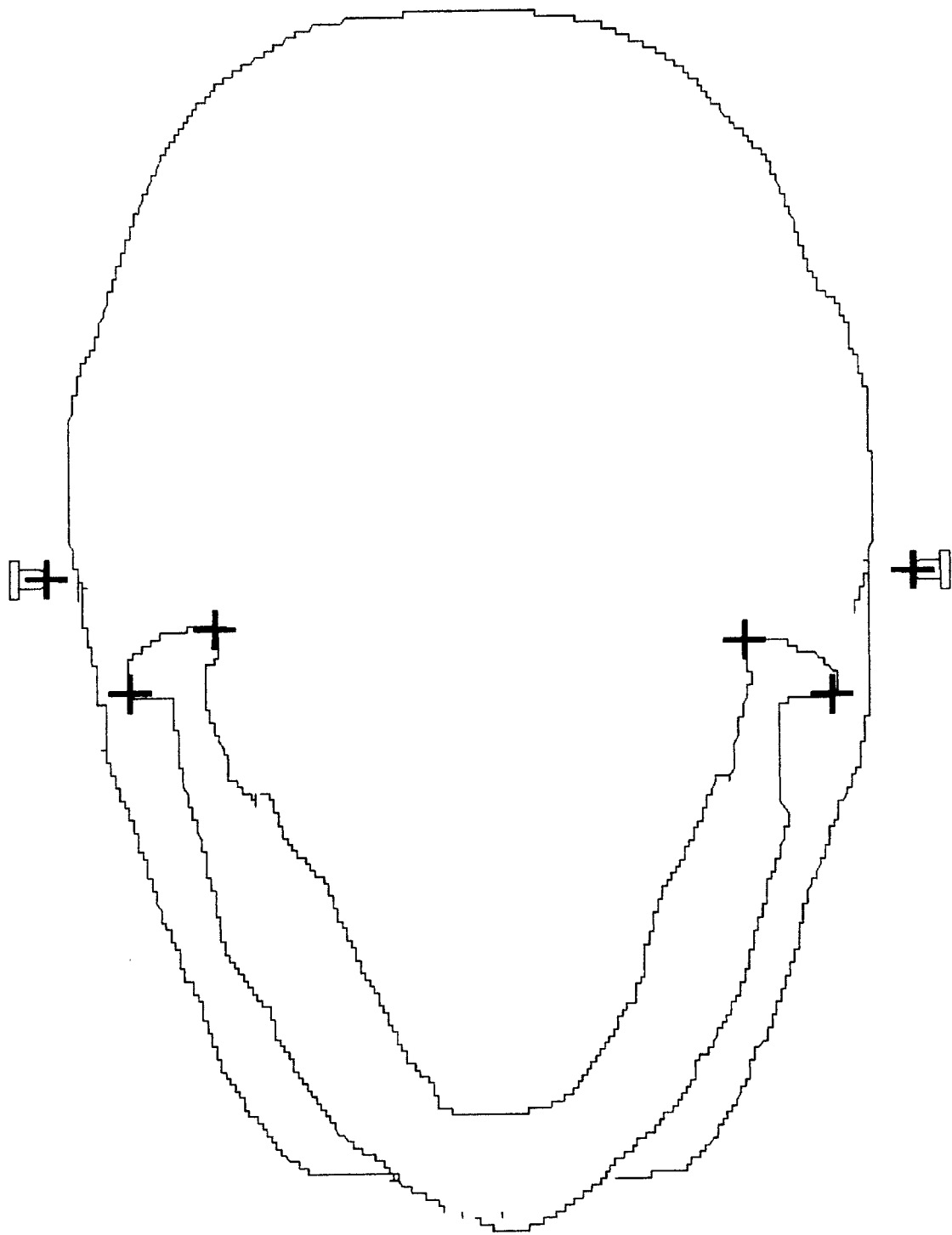
FIG. 15 is an illustration of the basal view with the six positions relative to the corrected projection of the left and right condyle.

FIG. 15 shows an exemplary basal view image projection. The six crosses on this figure denote the respective left and right ear posts, left and right condyle media and left and right condyle lateral. Position data for these six points are recorded and used by the controller in positioning the tomographic x-ray imaging apparatus.

Figure 16A:
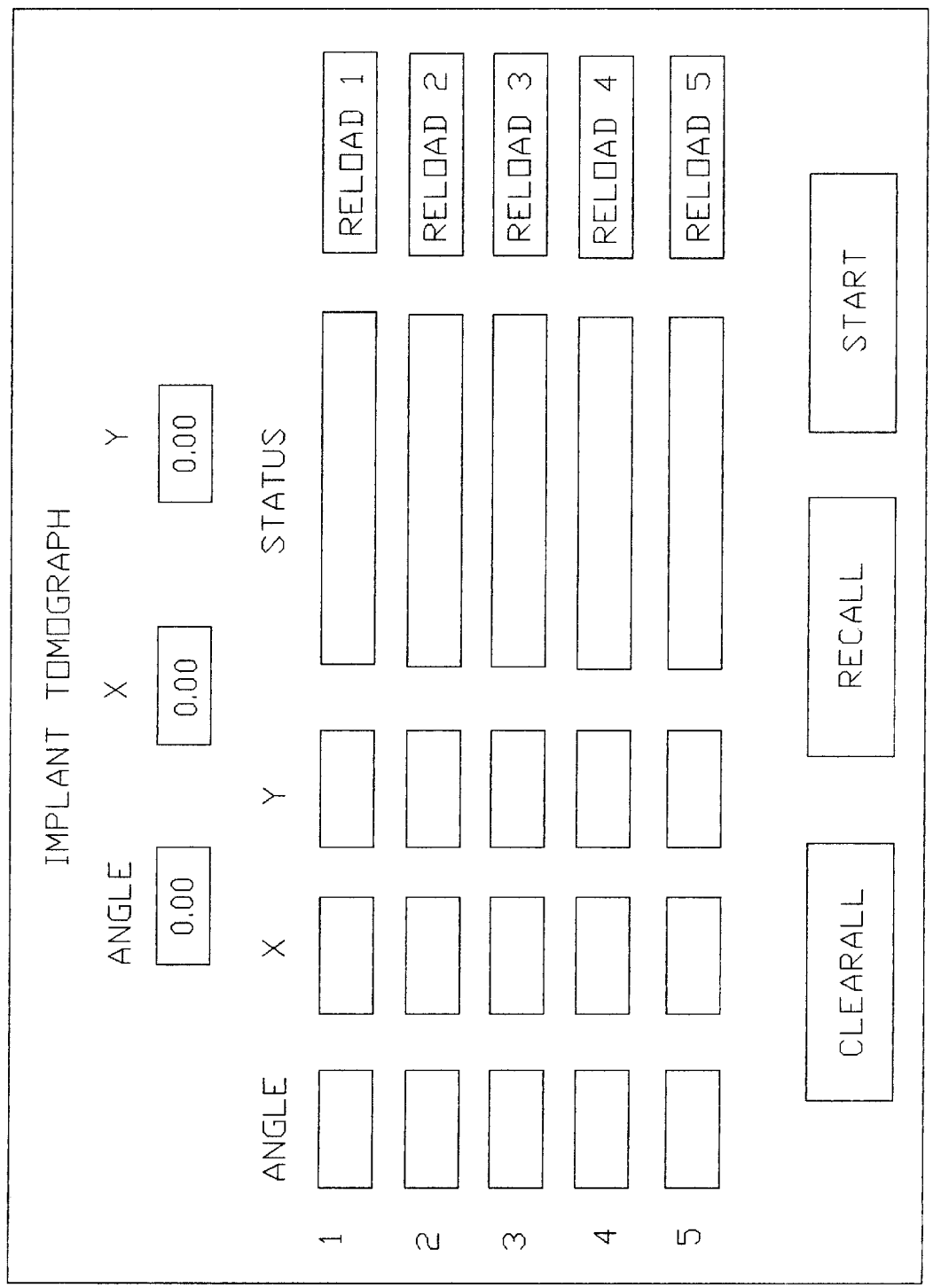
FIG. 16A is an illustration of the screen display presented by the controller to instruct the user on the input of the positional information for the implant modality.
Figure 16B:
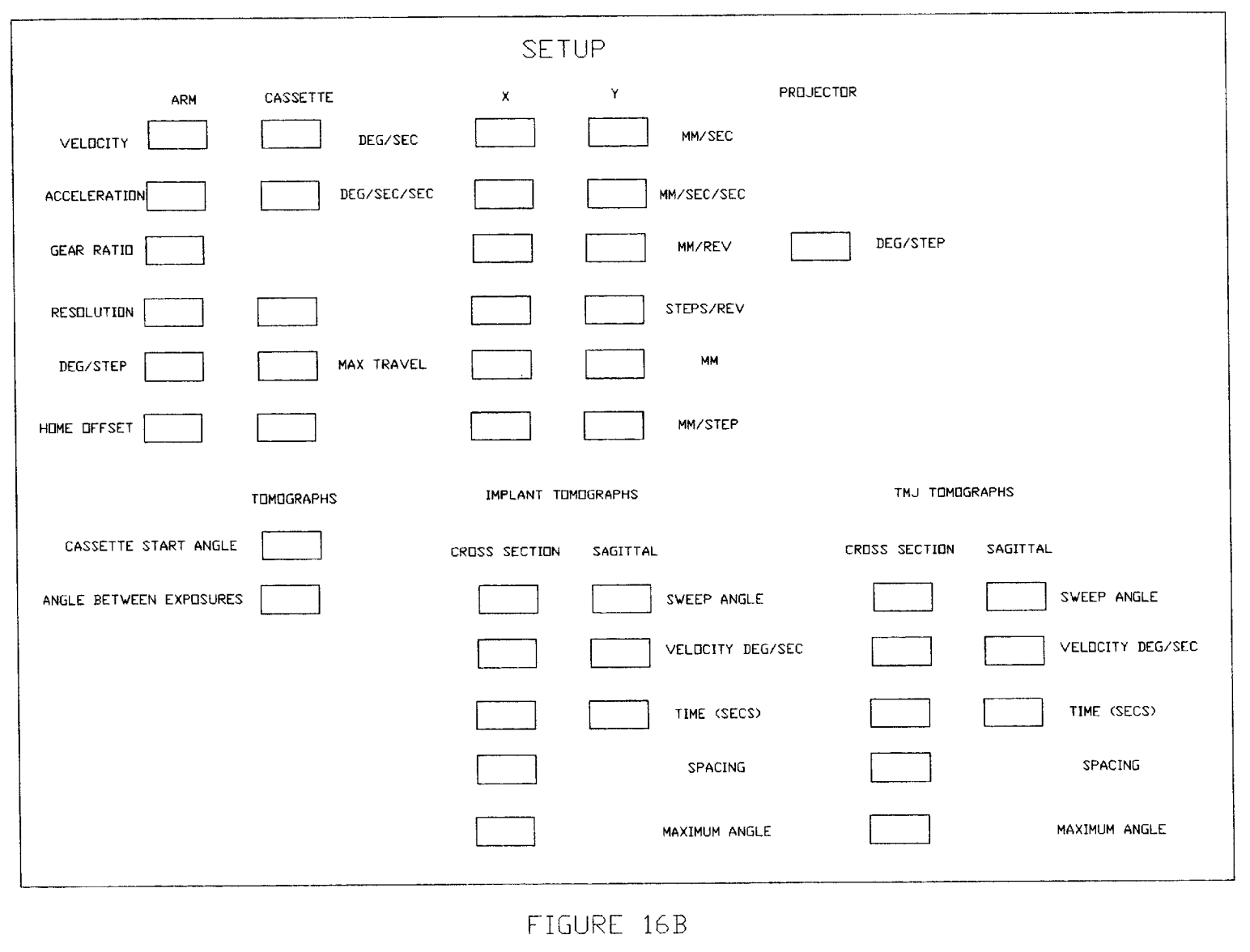
Figure 16C:
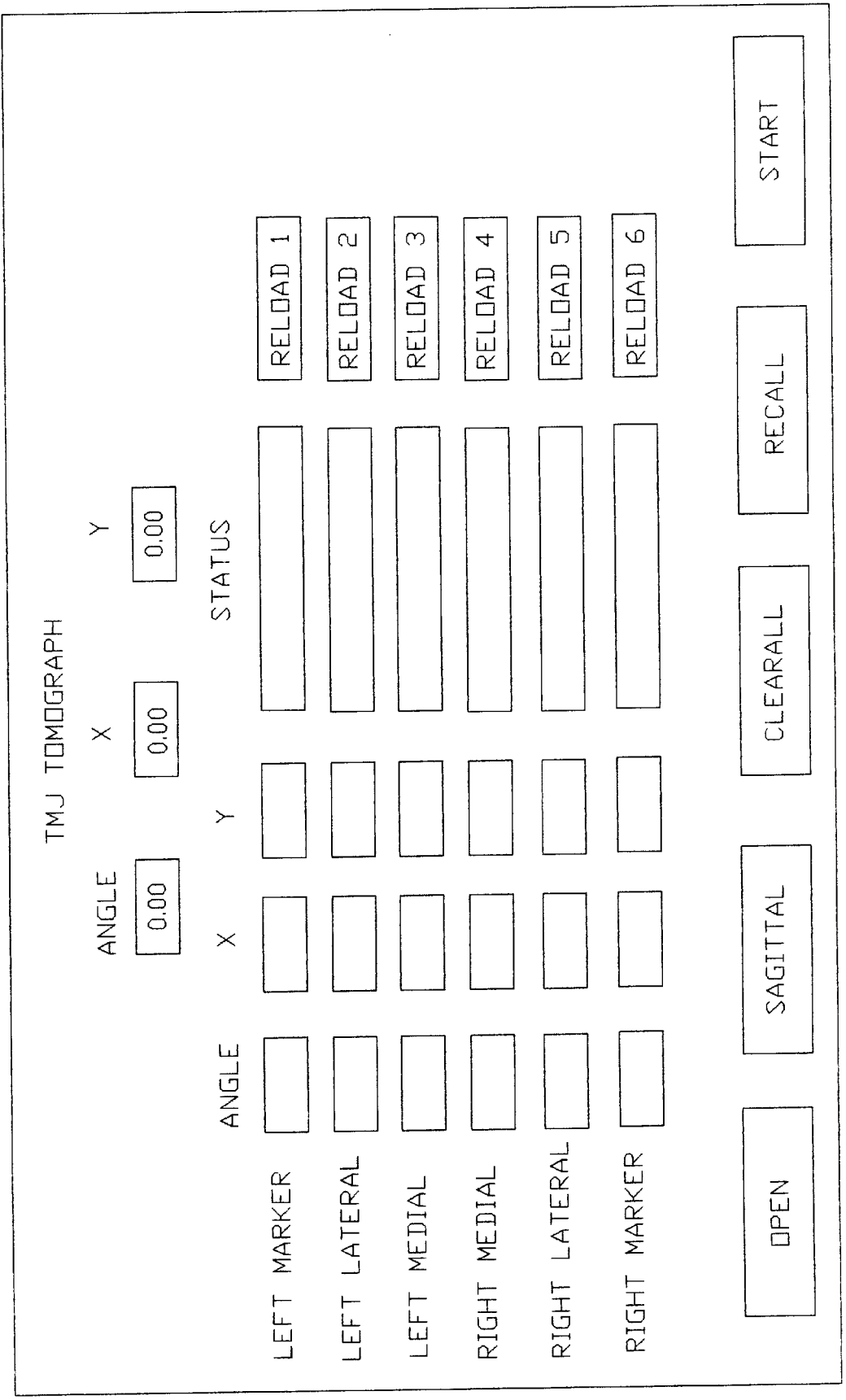
FIG. 16C is an illustration of the screen display presented by the controller to instruct the user on the input of the positional information for the TMJ modality.

In accordance with a preferred embodiment, the tomographic x-ray imaging apparatus includes a display screen for displaying instructions and status information to an operating clinician. Some exemplary screen displays presented to an operating clinician are shown in FIGS. 16A–16C. In particular, FIG. 16A illustrates the screen display that is presented by the controller to instruct the clinician on the input of the positional information for the implant modality. FIG. 16B illustrates the screen display presented by the controller for the setup sequence. FIG. 16C illustrates the screen display presented by the controller to instruct the user on the input of the positional information for the TMJ modality.

FIGS. 17A–17D are an explanation of the sequence of program operations for the implant modality as it is to be incorporated in the operating manual for the tomographic device. FIGS. 18A–18F are an explanation of the sequence of program operations for the TMJ modality as it is to be incorporated in the operating manual for the tomographic device.

Many modifications may be made to the preferred embodiment of the method and apparatus of the present invention as described above without departing from the spirit and the scope of the present invention.

For example, whilst the preferred embodiment of the apparatus includes the use of certain parts of a Villa Sistemi Medicali Rotograph it can readily be appreciated that the present invention is not so limited and any suitable apparatus may be used.

What is claimed is:

1. A method of accurately positioning a tomographic plane of an x-ray tomographic imaging apparatus to image multiple sites of interest on the mandible or maxilla of a patient without moving the head of the patient for each image exposure, the x-ray tomographic imaging apparatus comprising an x-ray source and an image receptor disposed opposite one another about a central vertical axis that is perpendicular to an x-ray beam emitted from the x-ray source and both being rotatable in an arc around the central vertical axis, the x-ray beam having a central axis that lies within a vertical plane which defines the tomographic plane of the x-ray imaging apparatus, and programmable positioning motors for providing translational and rotational movement to the x-ray source and image receptor relative to the central vertical axis, the method comprising the steps of:

a) forming a stent of the mandible and/or maxilla of the patient;

b) marking the stent at positions on the stent which corresponds to the sites of interest;

c) projecting a light beam vertically downwardly onto the stent;

d) positioning the tomographic imaging apparatus with regard to the stent so that:

i) the projected light beam is aligned with a first mark on the stent and also intersects a central x-ray beam axis of the tomographic imaging apparatus, the light beam thereby providing an indication of the tomographic plane of the tomographic imaging apparatus;

ii) a selected plane through the particular site of interest is perpendicular to the x-ray beam from an x-ray source;

e) recording positional data of the x-ray apparatus and image receptor in step d);

f) repeating steps d) through e) above for each site of interest that is marked on the stent;

g) positioning the head of the patient to engage the stent; and h) operating the tomographic imaging apparatus using the recorded positional data to accurately position the x-ray source and image receptor for taking an x-ray projection at each site of interest without moving the patient's head between successive projections and thereby eliminating repositioning errors associated with movement of the patient's head between exposures.

2. The method defined in claim 1, wherein the step of projecting a light beam includes projecting a cross having the first arm coincident with a central axis of the x-ray beam and a second arm co-planar with the tomographic plane of the x-ray imaging apparatus.

3. The method defined in claim 2, wherein for each site of interest includes the steps of:

a) projecting a first tomographic image of the site in a sagittal plane;

b) projecting three more tomographic images of the site in three cross-sectional planes, each spaced at a predetermined interval from one another; and c) aligning all four tomographic images so that the mandibular canal readily visualized in the sagittal plane can be positionally projected to adjacent cross-sectional tomographic projections of the site for evaluation of the positional accuracy of the x-ray tomographic imaging apparatus.

4. The method defined in claim 2, wherein the step of marking the stent includes using a radio opaque marker.

5. The method defined in claim 2, wherein the step of marking the stent includes inserting a metallic plug or ball into the stent at the site of interest.

6. The method defined in claim 2, which includes using a laser or incandescent light beam to project the cross.

7. The method defined in claim 2, wherein the step of positioning the tomographic x-ray imaging apparatus includes the step of aligning the first arm of the cross parallel with a tangent to the arc of the mandible or maxilla at the site of interest.

8. In combination, a tomographic x-ray imaging apparatus comprising an image receptor and an x-ray source being rotatable in an arc around a central axis perpendicular to an x-ray beam emitted from the x-ray source, the central axis lying within a vertical plane which defines a tomographic plane of the tomographic x-ray imaging apparatus, and an apparatus for positioning the tomographic x-ray imaging apparatus on the head of a patient accurately for tomographic x-ray imaging of a selected tomographic plane through a site of interest on the mandible or maxilla of the patient, the positioning apparatus comprising:

a) light source means for projecting a light beam vertically downwardly to intersect the central axis of the tomographic x-ray imaging apparatus, the light beam thereby providing an indication of the tomographic plane of the tomographic imaging apparatus;

b) a stent of the mandible or maxilla of a patient, said stent having a plurality of marks corresponding to particular sites of interest on the mandible or maxilla;

c) stent support means for holding the stent in position for alignment of said light beam with each of said plurality of marks on said stent such that when a patient is positioned to engage the stent and the x-ray imaging apparatus is operated to produce an x-ray image, the selected plane through each particular site of interest is perpendicular to the x-ray beam from the x-ray source;

d) positioning motor means for effecting X, Y and rotational positioning of said x-ray source and said image receptor with respect to said stent when engaged by said stent support means; and e) control means for recording position data for each site of interest and for accurately repositioning said x-ray source and said image receptor in relation to said stent for taking successive projections of each site of interest without moving the patient's head between successive projections of each site of interest.

9. The apparatus defined in claim 8, wherein:

said plurality of markings on said stent includes up to a total of five.

10. The apparatus defined in claims 9, wherein:

a) said light beam projected by said light source means is in the shape of a cross; and b) said light source means further includes rotation means for rotating said cross such that a first arm of said cross is coincident with a central axis of the x-ray beam from the x-ray source and a second arm of said cross is co-planar with the tomographic plane of the tomographic x-ray imaging apparatus.

11. The apparatus defined in claim 8, wherein the mark on the stent is a radio opaque marker.

12. The apparatus defined in claims 11, wherein:

a) said light beam projected by said light source means is in the shape of a cross; and b) said light source means further includes rotation means for rotating said cross such that a first arm of said cross is coincident with a central axis of the x-ray beam from the x-ray source and a second arm of said cross is co-planar with the tomographic plane of the tomographic x-ray imaging apparatus.

13. The apparatus defined in claim 8, wherein the radio opaque marker is a metallic ball inserted into the stent at the particular site of interest.

14. The apparatus defined in claims 8, wherein:

a) said light beam projected by said light source means is in the shape of a cross; and b) said light source means further includes rotation means for rotating said cross such that a first arm of said cross is coincident with a central axis of the x-ray beam from the x-ray source and a second arm of said cross is co-planar with the tomographic plane of the tomographic x-ray imaging apparatus.

15. The apparatus defined in claim 8, wherein the light source means comprises a laser.

16. The apparatus defined in claim 8, wherein the light source means comprises an incandescent source.

* * * * *